United States Patent
Xie et al.

(10) Patent No.: US 11,802,300 B2
(45) Date of Patent: Oct. 31, 2023

(54) GENETICALLY ENGINEERED STRAIN WITH HIGH YIELD OF L-VALINE AND METHOD FOR PRODUCING L-VALINE BY FERMENTATION

(71) Applicant: TIANJIN UNIVERSITY OF SCIENCE & TECHNOLOGY, Tianjin (CN)

(72) Inventors: Xixian Xie, Tianjin (CN); Heyun Wu, Tianjin (CN); Jiachu Wang, Tianjin (CN); Faqing Wu, Tianjin (CN); Xiaoqian Liu, Tianjin (CN); Yanan Hao, Tianjin (CN)

(73) Assignee: TIANJIN UNIVERSITY OF SCIENCE & TECHNOLOGY, Tianjin (CN)

(*) Notice: Subject to any disclaimer, the term of this patent is extended or adjusted under 35 U.S.C. 154(b) by 0 days.

(21) Appl. No.: 17/761,215

(22) PCT Filed: Oct. 30, 2019

(86) PCT No.: PCT/CN2019/114288
§ 371 (c)(1),
(2) Date: Mar. 17, 2022

(87) PCT Pub. No.: WO2021/077455
PCT Pub. Date: Apr. 29, 2021

(65) Prior Publication Data
US 2023/0107828 A1    Apr. 6, 2023

(30) Foreign Application Priority Data
Oct. 24, 2019  (CN) .......................... 201911016250.3

(51) Int. Cl.
| | |
|---|---|
| C12P 13/08 | (2006.01) |
| C12N 9/06 | (2006.01) |
| C12N 9/10 | (2006.01) |
| C12N 9/14 | (2006.01) |
| C12N 15/52 | (2006.01) |
| C12N 15/70 | (2006.01) |
| C12R 1/125 | (2006.01) |
| C12R 1/19 | (2006.01) |

(52) U.S. Cl.
CPC ............ *C12P 13/08* (2013.01); *C12N 9/0016* (2013.01); *C12N 9/1022* (2013.01); *C12N 9/14* (2013.01); *C12N 15/52* (2013.01); *C12N 15/70* (2013.01); *C12Y 104/01009* (2013.01); *C12Y 202/01006* (2013.01); *C12R 2001/125* (2021.05); *C12R 2001/19* (2021.05)

(58) Field of Classification Search
CPC ..... C12P 13/08; C12N 9/0016; C12N 9/1022; C12N 9/14; C12N 15/52; C12N 15/70; C12N 9/0004; C12Y 104/01009; C12Y 202/01006; C12Y 306/01005
See application file for complete search history.

(56) References Cited

FOREIGN PATENT DOCUMENTS

| | | |
|---|---|---|
| CN | 105296410 A | 2/2016 |
| CN | 106520651 A | 3/2017 |
| CN | 108913642 A | 11/2018 |
| WO | 2013175428 A2 | 11/2013 |

OTHER PUBLICATIONS

Annette Michalowski, et al., *Escherichia coli* HGT: Engineered for high glucose throughput even under slowly growing or resting conditions, Metabolic Engineering, 2017, pp. 93-103, vol. 40.
Ekaterina A. Savrasova, et al., Application of leucine dehydrogenase Bcd from Bacillus subtilis for L-valine synthesis in *Escherichia coli* under microaerobic conditions, Heliyon, 2019, pp. 1-25, vol. 5, Article No. e01406.
Satoshi Hasegawa, et al., Improvement of the Redox Balance Increases L-Valine Production by Corynebacterium glutamicum under Oxygen Deprivation Conditions, Applied and Environmental Microbiology, 2012, pp. 865-875, vol. 78, No. 3.
Jin Hwan Park, et al., Metabolic engineering of *Escherichia coli* for the production of L-valine based on transcriptome analysis and in silico gene knockout simulation, PNAS, 2007, pp. 7797-7802, vol. 104, No. 19.
Jaakko Soini, et al., Norvaline is accumulated after a down-shift of oxygen in *Escherichia coli* W3110, Microbial Cell Factories, 2008, pp. 1-14, vol. 7, No. 30.

(Continued)

*Primary Examiner* — Iqbal H Chowdhury
(74) *Attorney, Agent, or Firm* — Bayramoglu Law Offices LLC

(57) ABSTRACT

A genetically engineered strain having high-yield of L-valine is disclosed. Starting from *Escherichia coli* W3110, an acetolactate synthase gene alsS of *Bacillus subtilis* is inserted into a genome thereof and overexpressed; a ppGpp 3'-pyrophosphate hydrolase mutant R290E/K292D gene spoTM of *Escherichia coli* is inserted into the genome and overexpressed; a lactate dehydrogenase gene ldhA, a pyruvate formate lyase I gene pflB, and genes frdA, frdB, frdC, frdD of four subunits of fumaric acid reductase are deleted from the genome; a leucine dehydrogenase gene bcd of *Bacillus subtilis* replaces a branched chain amino acid transaminase gene ilvE of *Escherichia coli*; and an acetohydroxy acid isomeroreductase mutant L67E/R68F/K75E gene ilvCM replaces the native acetohydroxy acid isomeroreductase gene ilvC of *Escherichia coli*. Furthermore, the L-valine fermentation method is improved by using a two-stage dissolved oxygen control. The L-valine titer and the sugar-acid conversion rate are increased.

14 Claims, 7 Drawing Sheets
Specification includes a Sequence Listing.

(56) References Cited

OTHER PUBLICATIONS

Jin Hwan Park, et al., *Escherichia coli* W as a New Platform Strain for the Enhanced Production of L-Valine by Systems Metabolic Engineering, Biotechnology and Bioengineering, 2011, pp. 1140-1147, vol. 108, No. 5.

Yanan Hao, et al., High-yield production of L-valine in engineered *Escherichia coli* by a novel two-stage fermentation, Metabolic Engineering, 2020, pp. 198-206, vol. 62.

Yifan Li, et al., Metabolic engineering of *Escherichia coli* using CRISPR-Cas9 meditated genome editing, Metabolic Engineering, 2015, pp. 13-21, vol. 31.

Satoshi Hasegawa, et al., Engineering of Corynebacterium glutamicum for High-Yield L-Valine Production under Oxygen Deprivation Conditions, Applied and Environmental Microbiology, 2013, pp. 1250-1257, vol. 79, No. 4.

GENETICALLY ENGINEERED STRAIN WITH HIGH YIELD OF L-VALINE AND METHOD FOR PRODUCING L-VALINE BY FERMENTATION

CROSS REFERENCE TO THE RELATED APPLICATIONS

This application is the national phase entry of International Application No. PCT/CN2019/114288, filed on Oct. 30, 2019, which is based upon and claims priority to Chinese Patent Application No. 201911016250.3, filed on Oct. 24, 2019, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named "GBRSMJ027_Sequence_Listing_v2.txt", created on 06/20/2023, and is 39,245 bytes in size.

TECHNICAL FIELD

The disclosure relates to the field of microorganisms, the field of genetic engineering and the field of fermentation engineering, in particular to a genetically engineered strain with high yield of L-valine and application thereof.

BACKGROUND

L-valine, which is one of branched-chain amino acids (BCAA), has been widely used in food, medicine, cosmetics, feed, and other fields. As an essential amino acid for human body, it can not only promote muscle formation, strengthen liver function, and reduce muscle fatigue, but also serve as an intermediate for the synthesis of immune antibiotic drugs, and promote the synthesis of skin glial protein. In recent years, the demand for L-valine as an important amino acid in feed diet is continuously increasing.

Pyruvate is used as a direct precursor in the synthesis branch of L-valine. Pyruvate undergoes four steps of reaction catalyzed by acetolactate synthase, acetohydroxy acid isomeroreductase, dihydroxyacid dehydratase and branched-chain amino acid transaminase to finally produce L-valine. The modification of the strain for producing L-valine mainly focuses on the following aspects: (1) Removal of feedback inhibition of the final product on the synthesis rate-limiting enzyme. The key enzyme for the synthesis of L-valine from the key precursor pyruvate is acetolactate synthase, which is subjected to feedback-inhibition by three branched-chain amino acids, including L-valine, L-leucine, and L-isoleucine. (2) Increase of supply of reducing power NADPH. The reactions catalyzed by the acetohydroxy acid isomeroreductase and the branched chain amino acid transaminase are carried out by using NADPH as a coenzyme, so that increase of supply of the reducing power NADPH for the strain can improve L-valine synthesis efficiency. (3) Enhancement of product output. L-valine output requires a specific transporter on the cell membrane, and increased expression of the transporter contributes to the accumulation of L-valine.

At present, most of L-valine producing strains are *Corynebacterium glutamicum*. The genetic engineering of *Corynebacterium glutamicum* is relatively complex and requires a long period, making the strain modification difficult. In addition, the industrial strain of *Corynebacterium glutamicum* increases the metabolic flux of L-valine by overexpressing the key enzyme gene by the plasmid, but the plasmid has low stability and adversely affects the growth of bacterial cells, leading to prolonged fermentation cycle, which is not conducive to the industrial production of L-valine.

*E. coli* is another common strain for producing amino acids. *E. coli* has the advantages of well-defined genetic background and simple operation. In 2007, Park J H et al., introduced a mutated acetolactate synthase into *E. coli* W3110 to remove feedback inhibition to L-valine. Then, the global regulator Lrp and the transporter YgaZH were overexpressed, and the obtained strain could produce 7.61 g/L L-valine. In 2011, Park J H et al. overexpressed the genes ilvBN$^{mut}$, ilvCDE, ygaZH, and lrp in *E. coli* sub-strain W, which made the titer of L-valine up to 60.7 g/L. According to Xie Xixian et al., insertion of a gene alsS encoding *Bacillus subtilis* acetolactate synthase into *E. coli*, removed the feedback inhibition of L-valine on the synthetic pathway; meanwhile, insertion of a mutant gene spoT$^M$ for ppGpp 3'-pyrophosphate hydrolase mutant of *E. coli* enhanced pyruvate supply, and the obtained industrial strain VHY03 was subjected to 24 h shake-flask fermentation to produce 36 g/L L-valine. The present inventors found that, all the above strains adopt aerobic fermentation and have exuberant respiration, and excessive pyruvate is converted into $CO_2$ through tricarboxylic acid cyclic metabolism, so that the sugar-acid conversion rate is low, and the production cost of L-valine is high.

SUMMARY

One of the objectives of the present disclosure is to provide a new method for making an engineered strain for producing L-valine, which solves the problems of unbalanced coenzyme supply and demand and low sugar-acid conversion rate in L-valine anabolism and obtains an *E. coli* genetically engineered strain with high yield of L-valine through directional modification.

Another objective of the present disclosure is to produce L-valine using the *E. coli* genetically engineered strain through fermentation, which improves the process of controlling fermentation for production of L-valine by adopting two-stage dissolved oxygen control, thereby improving the L-valine titer and sugar-acid conversion rate.

The technical solution adopted by the present disclosure to achieve the above objectives is summarized as follows:

Starting from *E. coli* W3110, a *Bacillus subtilis* acetolactate synthase gene alsS is integrated into the genome of the *E. coli* W3110 and overexpressed; an *E. coli* ppGpp 3'-pyrophosphate hydrolase mutant R290E/K292D gene spoT$^M$ is integrated into the genome of the *E. coli* W3110 and overexpressed; a lactate dehydrogenase gene ldhA, a pyruvate formate lyase I gene pflB and genes frdA, frdB, frdC and frdD for four subunits of fumarate reductase are knocked out from the genome of the *E. coli* W3110; a branched-chain amino acid transaminase gene ilvE of *E. coli* is replaced with a leucine dehydrogenase gene bcd of *Bacillus subtilis*; and an acetohydroxy acid isomeroreductase gene ilvC of *E. coli* is replaced with an acetohydroxy acid isomeroreductase mutant L67E/R68F/K75E gene ilvC$^M$, thereby constructing a genetically engineered strain.

Identification of mutants in the present disclosure:
1. ppGpp 3'-pyrophosphate hydrolase mutant R290E/K292D, which represents that the mutant has mutations R290E/K292D and the amino acids at positions 290 and 292 are mutated, arginine (R) at position 290 is replaced by glutamic acid (E) and lysine (K) at position 292 is replaced by aspartic acid (D), wherein the position numbering corresponds to the amino acid sequence numbering of ppGpp 3'-pyrophosphate hydrolase in NCBI-Protein ID: NP_418107 shown in SEQ ID NO: 63. The mutant gene spoT$^M$ represents the encoding gene of the mutant R290E/K292D and is shown in SEQ ID NO: 64.

2. Acetohydroxy acid isomeroreductase mutant L67E/R68F/K75E, which represents that the mutant has mutations L67E/R68F/K75E and leucine (L) at position 67 is replaced with glutamic acid (E), arginine (R) at position 68 is replaced with phenylalanine (F), and lysine (K) at position 75 is replaced with glutamic acid (E), wherein the position numbering corresponds to the amino acid sequence numbering of acetohydroxy acid isomeroreductase ilvC in NCBI-Protein ID: NP_418222.1 shown in SEQ ID NO: 65. The mutant gene ilvC$^M$ represents the encoding gene of the mutant L67E/R68F/K75E and is shown in SEQ ID NO: 66.

In a further embodiment of the present disclosure, over-expression of the target gene can be achieve by replacing a strong promoter.

In a further embodiment of the present disclosure, the acetolactate synthase encoding gene alsS is integrated into a pseudogene ydeU site and controlled by a promoter $P_{trc}$.

In a further embodiment of the present disclosure, the ppgp 3'-pyrophosphate hydrolase mutant R290E/K292D gene spoT$^M$ is integrated into a pseudogene yeeP site and controlled by a promoter PVC.

In a further embodiment of the present disclosure, the ppGpp 3'-pyrophosphate hydrolase mutant R290E/K292D gene spoT$^M$ has a nucleotide sequence as shown in SEQ ID NO: 1.

In a further embodiment of the present disclosure, the encoding gene ilvC$^M$, the acetohydroxy acid isomeroreductase mutant L67E/R68F/K75E gene, has a nucleotide sequence as shown in SEQ ID NO: 2.

In a further embodiment of the present disclosure, the genetically engineered strain is constructed using a CRISPR/Cas9 mediated gene editing technology, which comprises step of:

(1) taking *E. coli* W3110 as a starting strain, constructing a junction fragment $P_{trc}$-alsS of a promoter $P_{trc}$ and an acetolactate synthase gene alsS, and integrating the junction fragment into a pseudogene ydeU site;

(2) constructing a junction fragment of a promoter $P_{trc}$ and a ppGpp 3'-pyrophosphate hydrolase mutant R290E/K292D gene spoT$^M$, and integrating the junction fragment into a pseudogene yeeP site;

(3) knocking out a lactate dehydrogenase gene ldhA, a pyruvate formate lyase I gene pflB and genes frdA, frdB, frdC and frdD for four subunit of fumarate reductase from the genome of the *E. coli* W3110;

(4) constructing a junction fragment $P_{trc}$-bcd of a promoter $P_{trc}$ and a leucine dehydrogenase gene bcd to replace a gene ilvE on the genome of the *E. coli* W3110;

(5) constructing a junction fragment $P_{trc}$-ilvC$^M$ of a promoter $P_{trc}$ and an encoding gene ilvC$^M$ of acetohydroxy acid isomeroreductase mutant to replace a gene ilvC on the genome of the *E. coli* W3110.

According to the method for producing L-valine by fermentation using one of above genetically engineered strain, a two-stage dissolved oxygen control process is adopted, wherein aerobic fermentation is carried out in the first stage of fermentation, and then anaerobic fermentation is carried out in the middle and later stages of fermentation, thereby improving the L-valine titer and sugar-acid-conversion rate.

Beneficial Effects:

Acetolactate synthase, a key enzyme for the synthesis of L-valine in *E. coli*, has insufficient activity and is subjected to feedback-inhibition caused by the product L-valine. The inventors of the present disclosure found that, introduction of natural acetolactate synthase from *Bacillus subtilis* provides the best effect in that this enzyme is insensitive to high-concentration L-valine, which can remarkably enhance the metabolic flow of the L-valine synthesis branch. Pyruvate is a direct precursor of L-valine, and the supply of pyruvate directly determines the yield of L-valine. The inventors of the present disclosure found that, overexpression of ppGpp 3'-pyrophosphate hydrolase mutant R290E/K292D can adjust the central metabolic flow, increase the intracellular concentration of pyruvate and thus improve the synthesis of L-valine. The catabolism of intracellular pyruvate is mainly achieved through pyruvate dehydrogenase to produce acetyl-CoA, and knocking out pyruvate dehydrogenase or reducing pyruvate dehydrogenase activity by mutation can reduce pyruvate decomposition but may seriously affect cell growth. By knocking out lactate dehydrogenase gene ldhA, pyruvate formate lyase I gene pflB and four fumarate reductase subunit genes frdA, frdB, frdC and frdD, the accumulation of byproducts (lactate, formate and succinate) under anaerobic conditions is reduced.

In the synthetic pathway of L-valine in *E. coli*, coenzyme NADPH is required when acetohydroxy acid isomeroreductase encoded by gene ilvC and branched-chain amino acid transaminase encoded by gene ilvE catalyze the reaction. Therefore, the supply of coenzyme NADPH is an important factor in the synthesis of L-valine. According to the present disclosure, replacement of the ilvE gene in *E. coli* with the leucine dehydrogenase encoding gene bcd of *Bacillus subtilis* and replacement the ilvC gene of *E. coli* with the mutant L67E/R68F/K75E gene ilvC$^M$ can change the coenzyme preference of the two enzymes, and as a result, NADH instead of NADPH is used as the coenzyme during synthesis of L-valine. Consequently, NADH produced in glycolytic pathway is oxidized to NAD$^+$ in L-valine anabolism to achieve coenzyme balance.

The synthesis of L-valine consumes NADH to produce NAD$^+$, so that it needs not to regenerate NAD$^+$ through the respiratory chain. According to the disclosure, fermentation of L-valine fermentation conducted using the mode of two-stage dissolved oxygen control is beneficial to improving sugar-acid conversion rate. Aerobic fermentation is carried out in the early stage of fermentation, during which the tricarboxylic acid cycle is active and the bacterial cells grow normally. When the bacterial cells are accumulated to a certain extent, anaerobic fermentation is carried out instead. In this stage, pyruvate is metabolized to generate L-valine, while consuming the NADH produced by glycolysis, thus ensuring the normal glycolysis of the cells. Under anaerobic conditions, tricarboxylic acid cycle is blocked, the growth of bacterial cells is stagnant, which can significantly reduce the consumption of pyruvate, and thus improve the sugar-acid conversion rate. In addition, anaerobic fermentation is adopted in that middle and late stages of fermentation, the agitation speed is reduced, and the use of sterile air is reduced, which can remarkably reduce fermentation energy consumption.

ydeU upstream homologous arm, 2: alsS target fragment, 3: ydeU downstream homologous arm, 4: integrated target fragment, 5: negative control, 6: fragment identified after junction.

Figure 2:
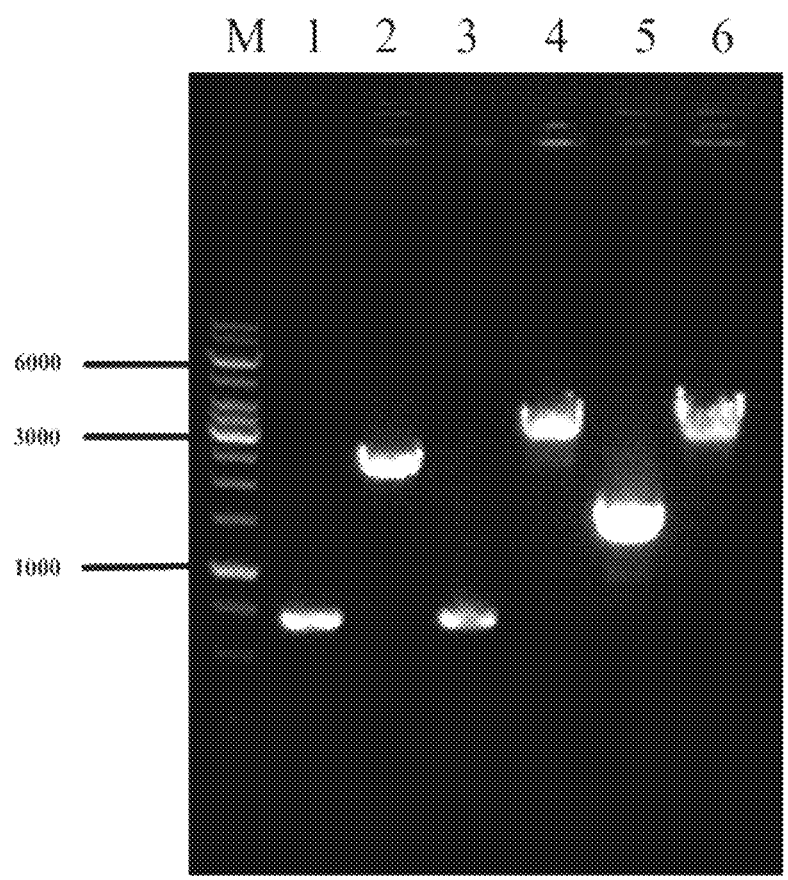

FIG. 2: Electrophoretogram for construction and verification of the junction fragment $P_{trc}$-spoT$^M$. M: Marker, 1: yeeP upstream homologous arm, 2: spoT$^M$ target fragment, 3: yeeP downstream homologous arm, 4: overlap fragment, 5: negative control, 6: fragment identified after junction.

Figure 3:
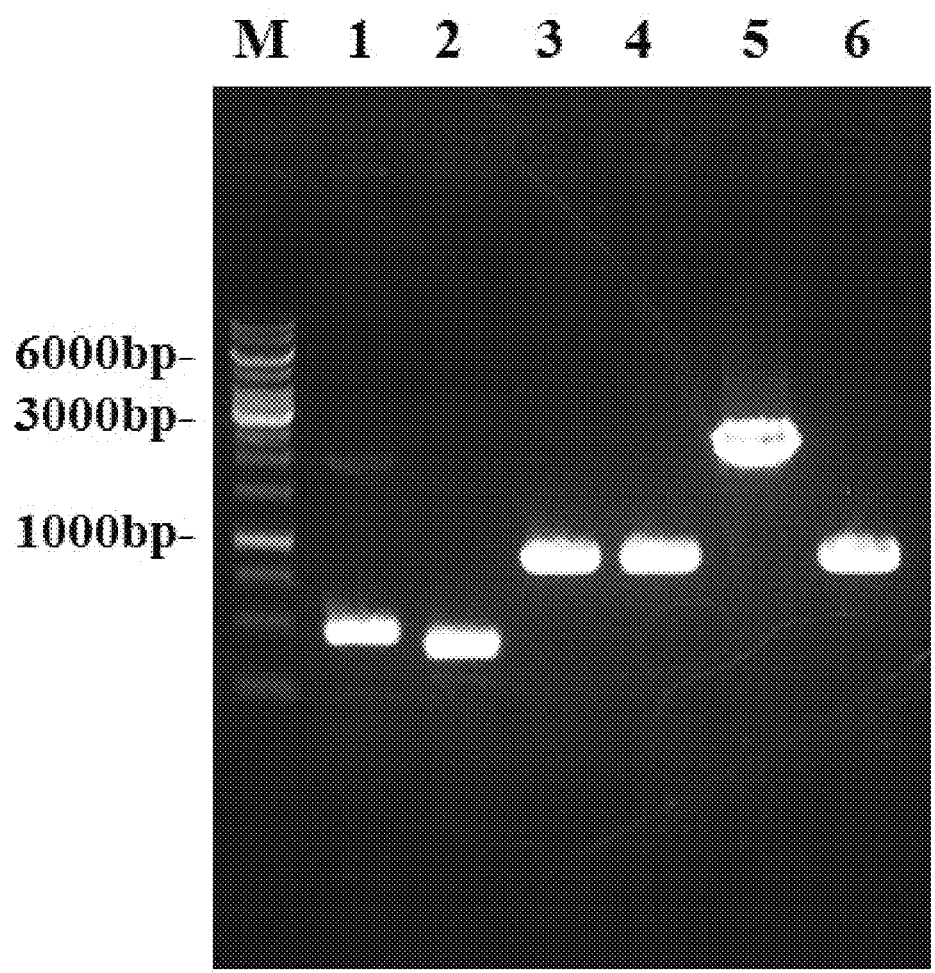

FIG. 3: Electrophoretogram for construction and verification of the fragment with ldhA gene knockout. M: Marker, 1: ldhA upstream homologous arm, 2: ldhA downstream homologous arm, 3: overlap fragment, 4: positive control, 5: negative control, 6: fragment identified after knockout.

Figure 4:
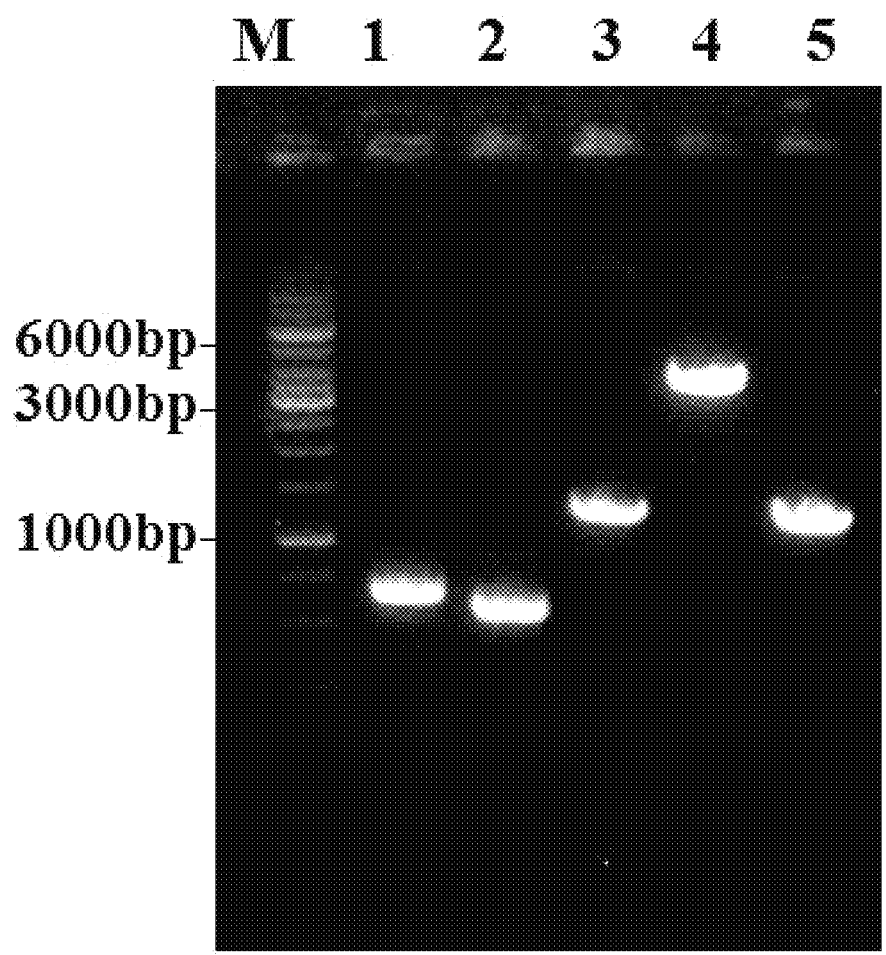

FIG. 4: Electrophoretogram for construction and verification of the fragment with pflB gene knockout. M: Marker, 1: pflB upstream homologous arm, 2: pflB downstream homologous arm, 3: overlap fragment, 4: negative control, 5: fragment identified after knockout.

Figure 5:
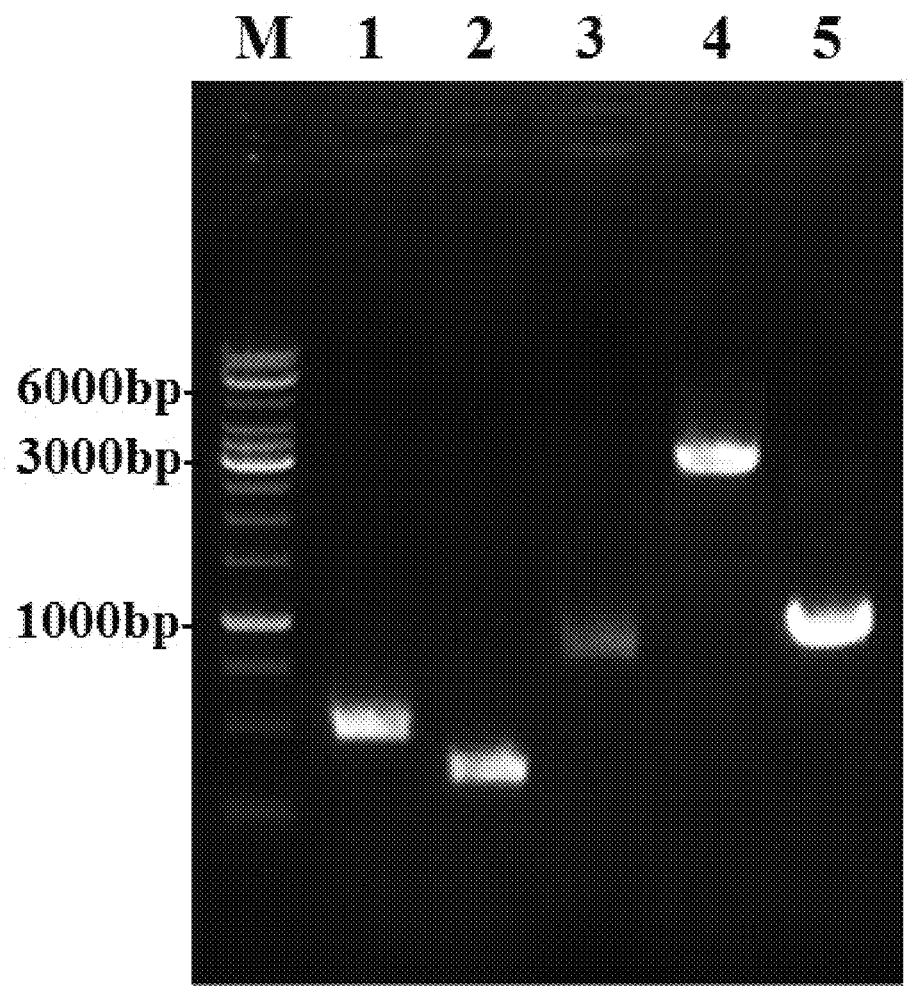

FIG. 5: Electrophoretogram for construction and verification of the fragment with frdABCD gene knockout. M: Marker, 1: frdABCD upstream homologous arm, 2: frdABCD downstream homologous arm, 3: overlap fragment, 4: negative control, 5: fragments identified after knockout.

Figure 6:
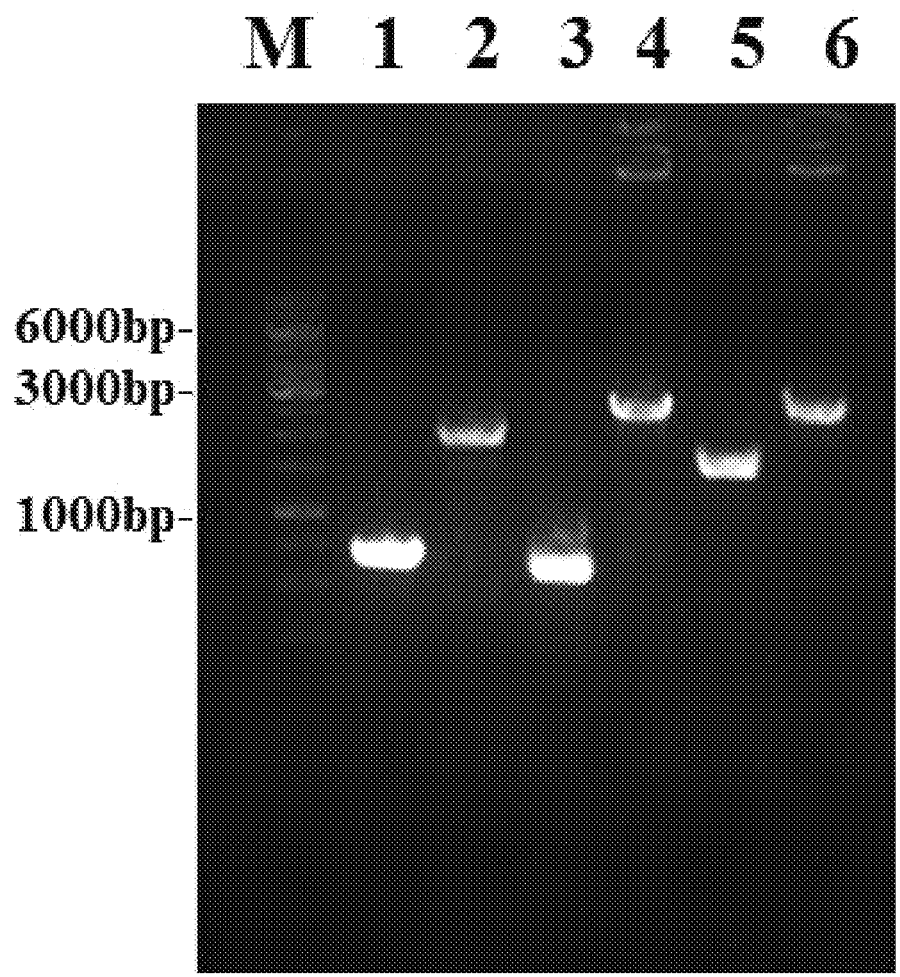

FIG. 6: Electrophoretogram for construction and verification of the junction fragment $P_{trc}$-bcd. M: Marker, 1: bcd upstream homologous arm, 2: bcd fragment, 3: bcd downstream homologous arm, 4: overlap fragment, 5: negative control, 6: fragment identified after junction.

Figure 7:
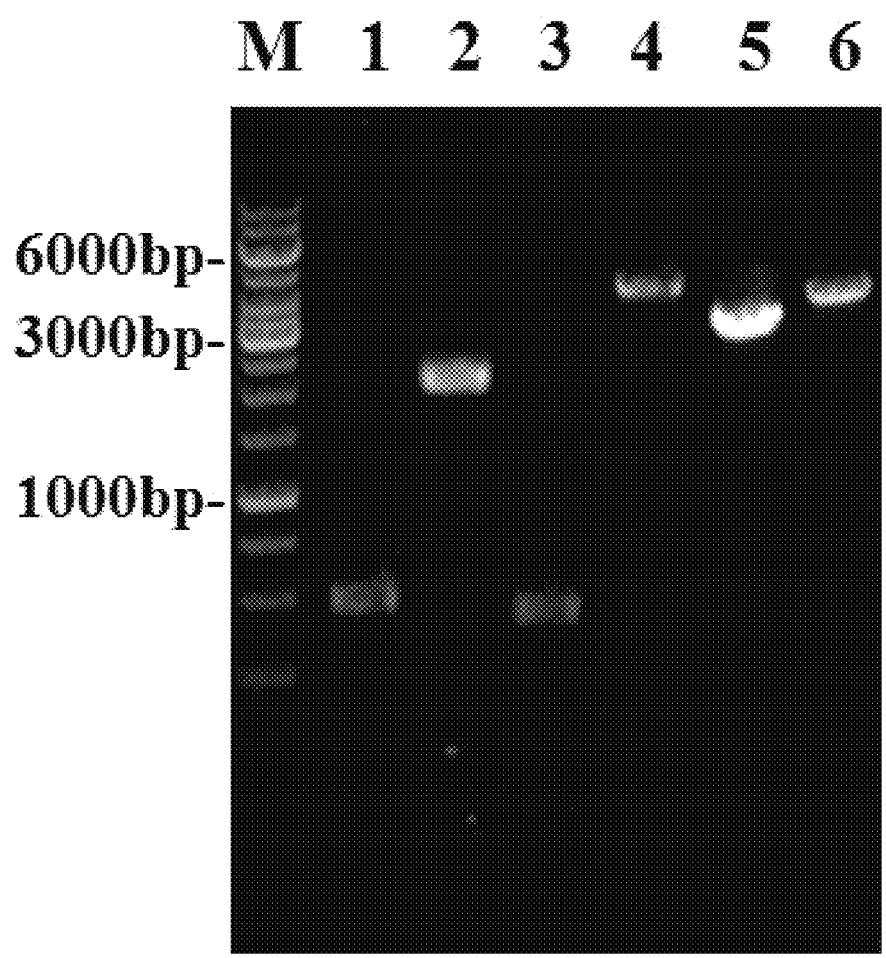

FIG. 7: Electrophoretogram for construction and verification of the junction fragment $P_{trc}$-ilvC$^M$. M: Marker, 1: ilvC$^M$ upstream homologous arm, 2: ilvC$^M$ fragment, 3: ilvC$^M$ downstream homologous arm, 4: overlap fragment, 5: negative control, 6: fragment identified after junction.

DETAILED DESCRIPTION OF THE EMBODIMENTS

The disclosure is described below by specific embodiments. Unless otherwise specified, the technical means used in the disclosure are methods well known to those skilled in the art. In addition, the embodiments are to be understood as illustrative rather than limiting the scope of the disclosure, and the spirit and scope of the disclosure are limited only by the claims. It will be apparent to those skilled in that art that various changes or modifications that are made to the composition and amounts of materials in these embodiments without departing from the spirit and scope of the disclosure are within the protection scope of the disclosure.

Example 1

Figure 1:
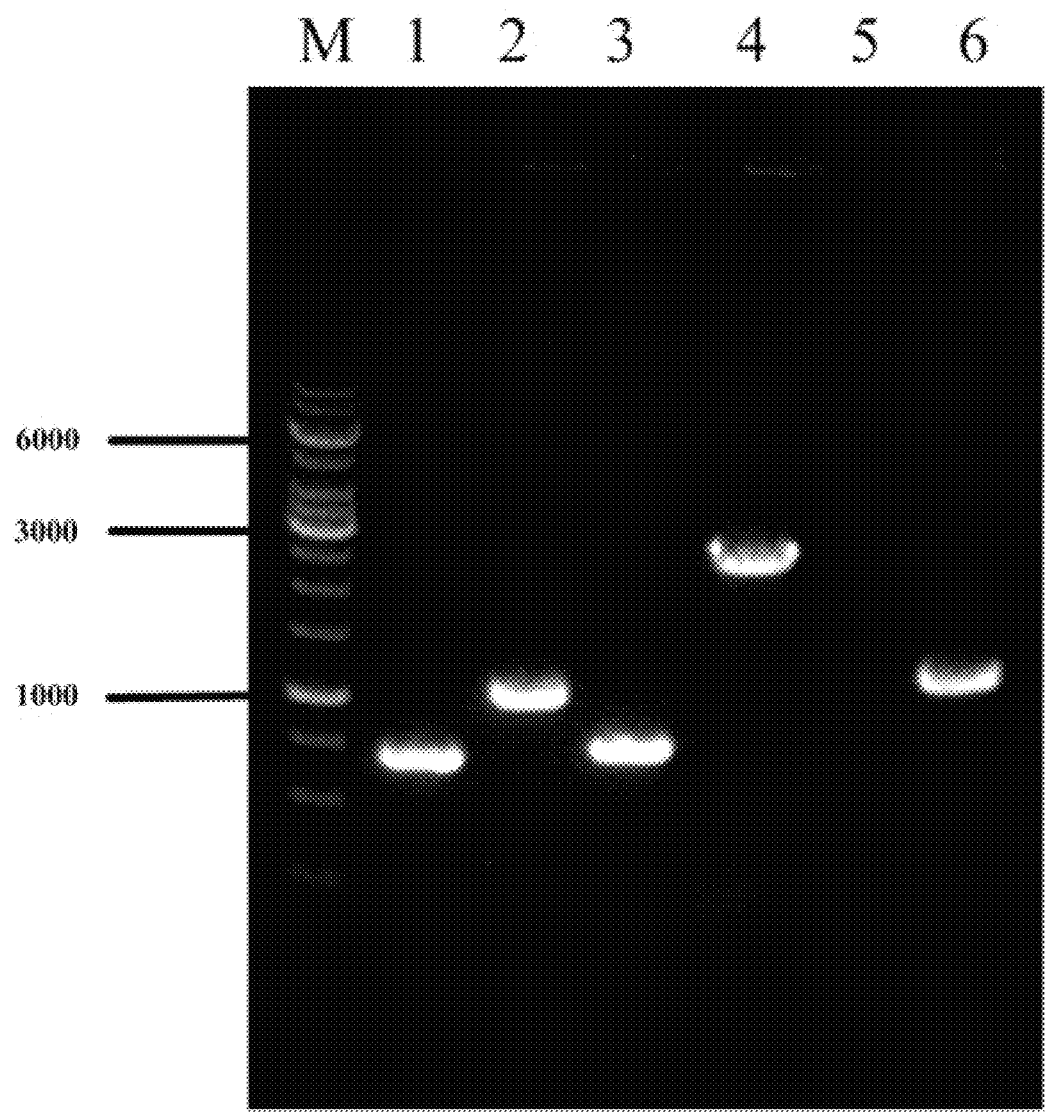
FIG. 1: Electrophoretogram for construction and verification of the junction fragment $P_{trc}$-alsS. M: Marker, 1.

Strains VXR01, VXR02 and VXR03 with high yield of L-valine were constructed by a gene editing method as described in the literature (Li Y, Lin Z, Huang C, et al. Metabolic engineering of *Escherichia coli* using CRISPR-Cas9 meditated genome editing. Metabolic engineering, 2015, 31: 13-21), which specifically comprises:

1. Construction of Strain VXR01 by Integrating Acetolactate Synthase Encoding Gene alsS into Pseudogene ydeU Site 1.1 Preparation of Recombinant DNA Fragments The alsS gene was integrated into the ydeU pseudogene locus. The gene alsS (NCBI-Protein ID: NP_391482.2) was obtained by PCR amplification using the genome of *B. subtilis* 168 as the template. Using *E. coli* W3110 genome as the template, ydeU upstream and downstream homologous arm fragments (primers UP-ydeU-S, UP-ydeU-A; DN-ydeU-S, DN-ydeU-A) were amplified. The promoter $P_{trc}$ was designed in the downstream primer of the upstream homologous arm and the upstream primer of the alsS gene. Overlap PCR was carried out using the upstream and downstream homologous arms and the target gene alsS as templates respectively to obtain integrated fragment $P_{trc}$-alsS (primers $P_{trc}$-alsS-S and $P_{trc}$-alsS-A). The electrophoretogram for construction of the integrated fragment $P_{trc}$-alsS and PCR verification of the positive strain is shown in FIG. 1. PCR conditions (Takara PrimeSTAR HS enzyme): pre-denaturation (95° C.) for 5 min; 30 cycles: denaturation (98° C.) for 10 s and annealing for 15 s; elongation at 72° C. for 10 min; cooling (4° C.). The upstream homologous arm UP-ydeU, the *E. coli* $P_{trc}$ promoter, the target fragment alsS, and the downstream homologous arm DN-ydeU were connected by overlap PCR. The PCR amplification and overlap PCR systems are shown in the following tables.

TABLE 1

PCR amplification system

| Component | Volume (50 µL) |
|---|---|
| DNA template (200 ng/µL) | 1 µL |
| Upstream primer (10 µmol/L) | 1 µL |
| Downstream primer (10 µmol/L) | 1 µL |
| dNTP mixture(10 mmol/L) | 4 µL |
| 5 × Buffer | 10 µL |
| HS enzyme (5 U/µL) | 0.5 µL |
| ddH$_2$O | 32.5 µL |

TABLE 2

Overlap PCR amplification system

| Component | Volume (50 µL) |
|---|---|
| Fragment template | 2 µL |
| Upstream homologous arm upstream primer (10 µmol/L) | 1 µL |
| Downstream homologous arm downstream primer (10 µmol/L) | 1 µL |
| dNTP mixture (10 mmol/L) | 4 µL |
| 5 × Buffer | 10 µL |
| HS enzyme (5 U/µL) | 0.5 µL |
| ddH$_2$O | 31.5 µL |

1.2 Construction of gRNA Plasmid

The purpose of constructing gRNA plasmid is to enable the complex of Cas9 protein and tracrRNA to identify the target site of the target gene through base pairing and PAM so as to break the target DNA double strands. The target sequence was designed using CRISPR RGEN Tools. The target sequence DNA fragment in the plasmid pGRB-ydeU was prepared by annealing the primers gRNA-ydeU-S and gRNA-ydeU-A. Reaction conditions: pre-denaturation at 95° C. for 5 min; annealing at 30-50° C. for 1 min. The annealing system is as follows:

TABLE 3

Annealing system

| Reaction system | Volume (20 µL) |
|---|---|
| Primer (10 µmol/L) | 10 µL |
| Reverse complement primer (10 µmol/L) | 10 µL |

The DNA fragment containing the target sequence was homologously recombined with the linearized vector pGRB. The recombinant system is shown in the following table. The recombinases used were those of CloneExpress® II One Step Cloning Kit series; recombination conditions: 37° C., 30 min.

TABLE 4

| Recombinant system | |
|---|---|
| Reaction system | Volume (10 μL) |
| 5 × CE II Buffer | 4 μL |
| Linearized vector | 1 μL |
| Insert fragment | 1 μL |
| Exnase ® II | 2 μL |
| ddH$_2$O | 2 μL |

The entire recombinant system was uniformly added into 100 μL of DH5a transformed competent cells, which were treated with ice bath for 30 min and incubate at 42° C. for 90 s, followed by the addition of 900 μL of resuscitation fluid for resuscitation at 37° C. for 1 h. After centrifuging at 8000 rmp for 2 min, part of the supernatant was discarded, and about 100 μL of bacterial cells was retained for resuspension, which was then uniformly coated on a plate containing ampicillin, and cultured overnight at 37° C. After single colonies grew out of the plate, positive recombinants were selected through colony PCR identification, plasmids were extracted and identified through enzyme digestion.

1.3 Electro-Transformation of Plasmids and Recombinant DNA Fragments

The pGRB-ydeU plasmid and the donor P$_{trc}$-alsS fragment were simultaneously electrotransformed to electrocompetent cells containing pREDCas9. The cells resuscitated after electrotransformation were plated on LB plates containing ampicillin and spectinomycin and incubated overnight at 32° C. Colony PCR was performed using identification primers (ydeU-identification-S, ydeU-identification-A) to screen for positive recombinants.

1.4 Elimination of Plasmids

Elimination of gRNA plasmid: The positive recombinants were cultured overnight in LB medium containing 0.2% arabinose, and then streaked in three regions on the LB plate containing spectinomycin resistance by the inoculation loop. The single colonies were selected and dispensed onto the LB plates containing ampicillin and spectinomycin respectively, and the single colonies that did not grow on the ampicillin plate but grew on the spectinomycin resistance plate were selected.

Elimination of pREDCas9 plasmid: The positive recombinants were transferred to LB liquid medium without resistance and cultured overnight at 42° C., and then streaked in three regions on the LB plate without resistance by the inoculation loop. The single colonies were selected and dispensed onto the LB plates containing spectinomycin and the LB plates without resistance respectively, and the single colonies that did not grow on the spectinomycin plate but grew on the plate without resistance were selected.

2. Construction of Strain VXR02 by Integrating Gene spoT$^M$ into Pseudogene yeeP Site 2.1 Preparation of Mutant Gene spoT$^M$ Primer design software primer5 was used, the genome of E. coli W3110 was used as the template (NCBI-Protein ID: BAE77643), the mutation site was designed in the downstream primer of the first fragment, and the gene spoT$^M$ encoding mutant was divided into two fragments for amplification (primers UP-spoT$^M$-S, up-spoT$^M$-A; DN-spoT$^M$-S, DN-spoT$^M$-A). Then, overlap PCR was performed by using the two fragments as templates to obtain mutant gene spoT$^M$ (primers UP-spoT$^M$-S and DN-spoT$^M$-A), with the nucleotide sequence being as set forth in SEQ ID NO: 1.

2.2 Preparation of Recombinant DNA Fragments

Using the genome of E. coli W3110 as the template, the yeeP upstream and downstream homologous arm fragments (primers UP-yeeP-S and UP-yeeP-A; DN-yeeP-S, DN-yeeP-A) were amplified. The promoter Pac was designed in the downstream primer of the upstream homologous arm and the upstream primer of the gene spoT$^M$. Then, overlap PCR was carried out using the upstream and downstream homologous arms and the target gene spoT$^M$ as templates (primers P$_{trc}$-spoT$^M$-S and P$_{trc}$-spoT$^M$-A). The electrophoretogram for construction of the integrated fragment P$_{trc}$-spoT$^M$ and PCR verification of the positive strain is shown in FIG. 2. The PCR amplification and overlap systems are the same as 1.1.

2.3 Construction of gRNA Plasmid

The target sequence DNA fragment in plasmid pGRB-yeeP was prepared by annealing of primers gRNA-yeeP-S and gRNA-yeeP-A, and the construction method is the same as that in 1.2.

2.4 Electro-Transformation of Plasmids and Recombinant DNA Fragments

The pGRB-yeeP plasmid and the donor P$_{trc}$-spoT$^M$ fragment were simultaneously electrotransformed into electrocompetent cells containing pREDCas9. The cells resuscitated after electrotransformation were plated on LB plates containing ampicillin and spectinomycin and incubated overnight at 32° C. Colony PCR was performed using the upstream primer of the upstream homologous arm and the downstream primer of the downstream homologous arm of the overlap fragments as identification primers to screen for positive recombinants.

2.5 Elimination of Plasmids

The method is the same as described in 1.4.

3. Construction of Strain VXR03 by Knockout of Genes ldhA, pflB, frdABCD 3.1 Preparation of Recombinant DNA Fragments With the genome of E. coli W3110 as the template, and based on the upstream and downstream sequences of the genes ldhA (NCBI-protein ID: NP_415898.1), pflB (NCBI-Protein ID: NP_415423.1) and frdABCD (NCBI-protein ID: NP_418578.1, NP_418577.1, NP_418576.1 and NP_418575.1), upstream homologous arm primers (U-ldhA-F, U-ldhA-R; U-pflB-F, U-pflB-R; U-frdABCD-F, U-frdABCD-R) and downstream homologous arm primers (D-ldhA-F, D-ldhA-R; D-pflB-F, D-pflB-R; D-frdABCD-F, D-frdABCD-R) were designed respectively. Then, overlap PCR was performed using the upstream and downstream homologous arms as templates to obtain genes ldhA, pflB and frdABCD knock-out fragments (upstream homologous arm-downstream homologous arm). Fragment with gene ldhA knockout, fragment with gene pflB knockout, fragment with genes frdABCD knock-out. The electrophoretogram for construction of the knockout fragments and PCR verification of the positive strain is shown in FIGS. 3-5, respectively. The PCR amplification and overlap systems are the same as those in 1.1.

3.2 Construction of gRNA Plasmid

Target sequence DNA fragments in plasmids pGRB-ldhA, pGRB-pflB, pGRB-frdABCD were prepared by annealing of primers (gRNA-ldhA-F, gRNA-ldhA-R; gRNA-pflB-F, gRNA-pflB-R; gRNA-frdABCD-F, gRNA-frdABCD-R), and the construction method is the same as in 1.2.

3.3 Electro-Transformation of Plasmids and Recombinant DNA Fragments

The plasmid and DNA fragment were co-electrotransformed into competent cells. The cells resuscitated after electrotransformation were plated on LB plates containing ampicillin and spectinomycin and incubated overnight at 32° C. Colony PCR was performed using the upstream prim of the upstream homologous arm and the downstream primer of the downstream homologous arm of the overlap fragments identification primers to screen for positive recombinants, and the bacterial cells were preserved.

3.4 Elimination of Plasmids

The method is the same as described in 1.4.

4. Construction of Strain VXR04 by Replacing the ilvE Gene of E. coli with the Leucine Dehydrogenase Encoding Gene Bcd of Bacillus subtilis 4.1 Preparation of Recombinant DNA Fragments The gene bcd (NCBI-protein ID: NP_390288.1) was obtained by PCR amplification using the genome of B. subtilis 168 as the template. Using the genome of E. coli W3110 as the template, upstream and downstream homologous arm fragments of gene ilvE (NCBI-Protein ID: YP_026247.1) were amplified (primers U-ilvE-F, U-ilvE-R; D-ilvE-F, D-ilvE-R). The promoter $P_{trc}$ was designed in the downstream primer of the upstream homologous arm and the upstream primer of the gene bcd. Overlap PCR was performed using the upstream and downstream homologous arms and the target gene bcd as templates, respectively, to obtain integration fragment $P_{trc}$-bcd (primers $P_{trc}$-bcd-F and $P_{trc}$-bcd-R). The electrophoretogram for construction of the integration fragment $P_{trc}$-bcd and PCR verification of the positive strain is shown in FIG. 6. The PCR amplification and overlap systems are the same as those in 1.1.

4.2 Construction of gRNA Plasmid

The target sequence DNA fragment in the plasmid pGRB-ilvE was prepared by annealing the primers gRNA-ilvE-F and gRNA-ilvE-R, and the construction method was the same as that in 1.2.

4.3 Electro-Transformation of Plasmids and Recombinant DNA Fragments

The pGRB-ilvE plasmid and the donor $P_{trc}$-bcd fragment were simultaneously electrotransformed into electro-competent cells containing pREDCas9. The cells resuscitated after electrotransformation were plated on LB plates containing ampicillin and spectinomycin and incubated overnight at 32° C. Colony PCR was performed using primers (U-ilvE-F, D-ilvE-R) to screen for positive recombinants.

4.4 Elimination of Plasmids

The method is the same as described in 1.4.

5. Construction of strain VXR05 by replacing the native ilvC gene with acetohydroxy acid isomeroreductase mutant gene $ilvC^M$ 5.1 Preparation of Mutant Gene $ilvC^M$ Primer design software primer5 was used, the genome of E. coli W3110 was used as the template (NCBI-Protein ID: NP_418222.1), mutation sites were designed in the downstream primer of the first fragment and the upstream primer of the second fragment, and the mutant gene to be amplified was divide into three fragments for amplification (primer 1-ilvC$^M$-F, 1-ilvC$^M$-R; 2-ilvC$^M$-F, 2-ilvC$^M$-R; 3-ilvC$^M$-F, 3-ilvC$^M$-R). Then, overlap PCR (primers 1-ilvC$^M$-F, 3-ilvC$^M$-R) was performed by using the two fragments as templates to obtain mutant gene ilvC$^M$, wherein the nucleotide sequence is as shown in SEQ ID NO: 2.

5.2 Preparation of Recombinant DNA Fragments

Using the genome of E. coli W3110 as the template, upstream and downstream homologous arm fragments of ilvC (NCBI-protein ID: NP_418222.1) were amplified (primers U-ilvC$^M$-F, U-ilvC$^M$R; D-ilvC$^M$-F, D-ilvC$^M$-R). The promoter $P_{trc}$ was designed in the downstream primer of the upstream homologous arm and the upstream primer of the mutant gene. Then, overlap PCR was performed using the upstream and downstream homologous arms and the mutant gene ilvC$^M$ as templates (primers U-ilvC$^M$-F, D-ilvC$^M$-R). The electrophoretogram for construction of the integration fragment $P_{trc}$-ilvC$^M$ and PCR verification of the positive strain is shown in FIG. 7. The PCR amplification and overlap systems are the same as 1.1.

5.3 Construction of gRNA Plasmid

The target sequence DNA fragment in the plasmid pGRB-ilvC was prepared by annealing the primers gRNA-ilvC-F and gRNA-ilvC-R, and the construction method is the same as that in 1.2.

5.4 Electro-Transformation of Plasmids and Recombinant DNA Segments

The pGRB-ilvC plasmid and the donor P-ilvC$^M$ fragment were simultaneously electrotransformed into electro-competent cells containing pREDCas9. The cells resuscitated after electrotransformation were plated on LB plates containing ampicillin and spectinomycin and incubated overnight at 32° C. Colony PCR was performed using the upstream primer of the upstream homologous arm and the downstream primer of the downstream homologous arm of the overlap fragment as identification primers to screen for positive recombinants.

5.5 Elimination of Plasmids

The method is the same as described in 1.4.

6. The Primers Involved in the Construction of the Above Strains are Shown in the Following Table.

TABLE 5

| Primer | Sequence (5'-3') | SEQ ID NO: |
|---|---|---|
| UP-spoT$^M$-S | TTGTATCTGTTTGAAAGCCTGAATC | 3 |
| UP-spoT$^M$-A | TCGCTTTTGGAATGGCGATATAGTCATCCACTTCGCCCG | 4 |
| DN-spoT$^M$-S | CGGGCGAAGTGGATGACTATATCGCCATTCCAAAAGCGA | 5 |
| DN-spoT$^M$-A | TTAATTTCGGTTTCGGGTGACT | 6 |
| UP-ydeU-S | CTGCGTAATAGCATAAGCGGG | 7 |
| UP-ydeU-A | AATTGTTATCCGCTCACAATTCCACACATTATACGAGCCG GATGATTAATTGTCAAGCTATTCATTTGAACCGTGCC | 8 |

TABLE 5-continued

Primers

| Primer | Sequence (5'-3') | SEQ ID NO: |
|---|---|---|
| P$_{trc}$-alsS-S | TCCGGCTCGTATAATGTGTGGAATTGTGAGCGGATAACAATTTCACACAGGAAACAGACCTTGACAAAAGCAACAAAGAACA | 9 |
| P$_{trc}$-alsS-A | ATTCCCCCACAGGCTAAGGTCTAGAGAGCTTTCGTTTTCATGAGT | 10 |
| DN-ydeU-S | ACTCATGAAAACGAAAGCTCTCTAGACCTTAGCCTGTGGGGGAAT | 11 |
| DN-ydeU-A | ATGTCGTGAGCGTGGTATTGTC | 12 |
| gRNA-ydeU-S | AGTCCTAGGTATAATACTAGTGTTCGGGTTGATAACATTGGGTTTTAGAGCTAGAA | 13 |
| gRNA-ydeU-A | TTCTAGCTCTAAAACCCAATGTTATCAACCCGAACACTAGTATTATACCTAGGACT | 14 |
| ydeU-identification-S | ACTGCGTAATAGCATAAGCGGG | 15 |
| ydeU-identification-A | TGCTTGCCGACCCCTGAGA | 16 |
| UP-yeeP-S | GGTCAGGAGGTAACTTATCAGCG | 17 |
| UP-yeeP-A | AATTGTTATCCGCTCACAATTCCACACATTATACGAGCCGGATGATTAATTGTCAAATGGCAGGGCTCCGTTTT | 18 |
| P$_{trc}$-spoT$^M$-S | TCCGGCTCGTATAATGTGTGGAATTGTGAGCGGATAACAATTTCACACAGGAAACAGACCTTGTATCTGTTTGAAAGCCTGAATC | 19 |
| P$_{trc}$-spoT$^M$-A | AGACCCGTTTAGAGGCCCCAAGGGGTTATGCTAGTTAATTTCGGTTTCGGGTGACT | 20 |
| DN-yeeP-S | TGGGGCCTCTAAACGGGTCTTGAGGGGTTTTTTGGAACTGGATTTTCTTCTGAACCTGT | 21 |
| DN-yeeP-A | ACGATGTCAGCAGCCAGCA | 22 |
| gRNA-yeeP-S | AGTCCTAGGTATAATACTAGTACAGAATATTCGCGAAAAAACGGGTTTTAGAGCTAGAA | 23 |
| gRNA-yeeP-A | TTCTAGCTCTAAAACCCGTTTTTTCGCGAATATTCTGTACTAGTATTATACCTAGGACT | 24 |
| U-ilvE-F | GGAACGATACAGCGAAACCAC | 25 |
| U-ilvE-R | AATTGTTATCCGCTCACAATTCCACACATTATACGAGCCGGATGATTAATTGTCAAGCTTTCTTCGTGGTCATTTTTAT | 26 |
| D-ilvE-F | CCACAGTGTATTAAGCAGACGTTAAATACAAAAAATGGGACGGCAC | 27 |
| D-ilvE-R | TGGGAGTCAGATACTTTCGGGT | 28 |
| P$_{trc}$-hed-F | TCCGGCTCGTATAATGTGTGGAATTGTGAGCGGATAACAATTTCACACAGGAAACAGACCTCTGAAGAATACACACATTAGGAGGA | 29 |
| P$_{trc}$-bcd-R | GTGCCGTCCCATTTTTTGTATTTAACGTCTGCTTAATACACTGTGG | 30 |
| gRNA-ilvE-F | AGTCCTAGGTATAATACTAGTCGCCAAAATCTATCGCTTCCGTTTTAGAGCTAGAA | 31 |
| gRNA-ilvE-R | TTCTAGCTCTAAAACGGAAGCGATAGATTTTGGCGACTAGTATTATACCTAGGACT | 32 |
| U-ilvC$^M$-F | TCTACCGACACCTGATTACGCAC | 33 |
| U-ilvC$^M$-R | AATTGTTATCCGCTCACAATTCCACACATTATACGAGCCGGATGATTAATTGTCAAATGGTGATTCCTCGTGATGTTGT | 34 |

TABLE 5-continued

| Primer | Sequence (5'-3') | SEQ ID NO: |
|---|---|---|
| D-ilvC-F | ACTTGATGACCGCCCTCTGTATTTTCGGTCTTCTCTCTCTGATTT | 35 |
| D-ilvC-R | ATAACAATGGGCAAAAATACGGT | 36 |
| 1-ilvC$^M$-F | TCCGGCTCGTATAATGTGTGGAATTGTGAGCGGATAACAATTTCACACAGGAAACAGACCATGGCTAACTACTTCAATACACT | 37 |
| 1-ilvC$^M$-R | GCGCGCTCCTCGGCAATCGCTTCTTTAAACTCAGCGTAGGAGATATCG | 38 |
| 2-ilvC$^M$-F | TGGTCTCGATATCTCCTACGCTGAGTTTAAAGAAGCGATTGCCGAGGAGCGCGC | 39 |
| 2-ilvC$^M$-R | CACCGACAAACAACAGATAAAACGAAAGGCCCAGTCTTTCGACTGAGCCTTTCGTTTTATTTGTCGGGGTGAGGGCATCAG | 40 |
| 3-ilvC$^M$-F | AAAGACTGGGCCTTTCGTTTTATCTGTTGTTTGTCGGTGAACGCTCTCCTGAGTAGGACAAATCCCTCTCCCACAGGGAGAGG | 41 |
| 3-ilvC$^M$-R | AAATCAGAGAGAGAAGACCGAAAATACAGAGGGCGGTCATCAAGT | 42 |
| gRNA-ilvC-F | AGTCCTAGGTATAATACTAGTTGGTCGCGAGTGGTTGATAAGTTTTAGAGCTAGAA | 43 |
| gRNA-ilvC-R | TTCTAGCTCTAAAACTTATCAACCACTCGCGACCAACTAGTATTATACCTAGGACT | 44 |
| U-ldhA-F | GCGGCTGGGATGTGAAAG | 45 |
| U-ldhA-R | GAATACGCCAAAGGACTCGTTCACCT | 46 |
| D-ldhA-F | TTTGGCGTATTCCGTCGCCTGTCTGC | 47 |
| D-ldhA-R | ATGTCTGTTTTGCGGTCGC | 48 |
| gRNA-ldhA-F | AGTCCTAGGTATAATACTAGTAAACGATGACGGCAGCCGCCGTTTTAGAGCTAGAA | 49 |
| gRNA-ldhA-R | TTCTAGCTCTAAAACGGCGGCTGCCGTCATCGTTTACTAGTATTATACCTAGGACT | 50 |
| U-pflB-F | TCGGCAACATTATCGGTGG | 51 |
| U-pflB-R | GGTTCATTTACGGCAACGCAGGATG | 52 |
| V-pflB-V | CGTAAATGAACCGTGAAATGCTGCTC | 53 |
| D-pflB-R | GGCGATAGGTCACCACTTCC | 54 |
| gRNA-pflB-F | AGTCCTAGGTATAATACTAGTTGTTCTCTGGCGACCCGATCGTTTTAGAGCTAGAA | 55 |
| gRNA-pflB-R | TTCTAGCTCTAAAACGATCGGGTCGCCAGAGAACAACTAGTATTATACCTAGGACT | 56 |
| U-frdABCD-F | GGTCTTCTTCGGTATCAGCAACA | 57 |
| U-frdABCD-R | TAGCAGCCAGACCGTAGAAAACCCTTCGTGCCCTTGTCAAAAACT | 58 |
| D-frdABCD-F | AGTTTTTGACAAGGGCACGAAGGGTTTTCTACGGTCTGGCTGCTA | 59 |

TABLE 5-continued

Primers

| Primer | Sequence (5'-3') | SEQ ID NO: |
|---|---|---|
| D-frdABCD-R | ACGCCAGTAAATGTTTTGCTGAC | 60 |
| gRNA-frdABCD-R | AGTCCTAGGTATAATACTAGTCCCAACCGAAATGACCCAACGTTTTAGAGCTAGAA | 61 |
| gRNA-frdABCD-R | TTCTAGCTCTAAAACGTTGGGTCATTTCGGTTGGGACTAGTATTATACCTAGGACT | 62 |

Example 2

Shake-Flask Fermentation of Strains VXR02 and VXR05:

Slant culture: the strain preserved at −80° C. was streak-inoculated on the activation slant, cultured at 37° C. for 12 h, and passaged two times.

Shake-flask seed culture: two loops of the seed strain on the slant were scraped using an inoculation loop and inoculated into a 500 mL triangular flask containing 30 mL of a seed culture medium, and cultured at 37° C. and 200 rpm for 8-10 h.

Shake-flask aerobic fermentation: with an inoculum size of 10-15%, seed fermentation broth was inoculated into a 500 mL triangular flask (final volume, 30 mL) filled with a fermentation medium, and shake-cultured at 37° C. and 200 r/min; the pH was maintained at 6.7-7.0 by adding ammonia in the process of fermentation, and a 60% (m/v) glucose solution was added to maintain the fermentation; the fermentation cycle was 24 h.

Aerobic-anaerobic two-stage fermentation: with an inoculum size of 10-15%, the seed fermentation broth was inoculated into a 500 mL triangular flask filled with a fermentation medium (final volume, 30 mL), and shake-cultured at 37° C. and 200 r/min; 12-16 h later, the bacterial solution was transferred to a 30 mL sealed flask isolated from the air, and shake-cultured at 37° C. and 200 r/min for 8-12 h; the total fermentation cycle was 24 h.

The slant medium comprised 5 g/L glucose, 10 g/L peptone, 10 g/L beef extract, 5 g/L yeast powder, 2.5 g/L NaCl, and 21-25 g/L agar, pH 7.0-7.2.

The seed culture medium comprised 18 g/L glucose, 1% yeast powder, 0.6% peptone, 0.12% $KH_2PO_4$, 0.05% $MgSO_4 \cdot 7H_2O$, 10 mg/L $FeSO_4 \cdot 7H_2O$, 10 mg/L $MnSO_4 \cdot H_2O$, 1.3 mg/L $V_{B1}$, 0.3 mg/L $V_H$, 20 ml/L phenol red, and two drops of a defoaming agent, initial pH 7.0-7.2.

The fermentation medium comprised 18 g/L glucose, 1 g/L yeast powder, 2 g/L peptone, 2 g/L $KH_2PO_4$, 1 g/L sodium citrate, 0.7 g/L $MgSO_4 \cdot 7H_2O$, 100 mg/L $FeSO_4 \cdot 7H_2O$, 100 mg/L $MnSO_4 \cdot H_2O$, 0.8 mg/L $V_{B1}$, 0.3 mg/L $V_H$, 20 mL/L phenol red, and two droplets of a defoaming agent, initial pH 7.0-7.2.

TABLE 6

Comparison of L-valine titer and conversion rate between shake-flask aerobic fermentation and aerobic-anaerobic two-stage fermentation

| | Aerobic fermentation | | Aerobic-anaerobic two-stage fermentation | |
|---|---|---|---|---|
| Strain | L-valine titer (g/L) | Sugar-acid conversion rate (%) | L-valine titer (g/L) | Sugar-acid conversion rate (%) |
| VXR02 | 40.1 | 29.2 | 25.1 | 27.5 |
| VXR05 | 41.4 | 30.0 | 42.7 | 36.3 |

As shown in Table 6, for the Aerobic fermentation mode, the L-valine titer and sugar-acid conversion rate of strain VXR05 were comparable to those of strain VXR02 in the Aerobic fermentation. For the aerobic-anaerobic two-stage fermentation mode, the titer of the strain VXR02 was remarkably reduced, indicating that the strain VXR02 cannot accumulate L-valine under the anaerobic condition. In contrast to the strain VXR02, the L-valine titer of VXR05 in the two-stage fermentation mode was higher than that in the aerobic fermentation mode, indicating that VXR05 can accumulate L-valine under anaerobic conditions. More beneficially, the sugar-acid conversion rate of VXR05 in the two-stage fermentation mode is remarkably increased by 21% compared with aerobic fermentation.

Example 3

Fermentation of VXR02 and VXR05 in 5 L Fermentor:

Aerobic fermentation: the strain was activated on the slant for two generations, and inoculated with an inoculum size of 15-20% into a fermentation medium to perform a fermentation. In the fermentation, the pH was controlled at about 6.7 and the temperature was maintained at 35° C., and the dissolved oxygen was controlled at 25-30%. After the glucose in the fermentation medium was depleted, an 80% (m/v) of glucose solution was fed to maintain the glucose concentration in the fermentation medium at 0.1-5 g/L; the fermentation cycle was 40 h.

Aerobic-anaerobic two-stage fermentation: the strain was activated on the slant for two generations, and inoculated with an inoculum size of 15-20% into a fermentation medium to perform a fermentation. In the fermentation, the pH was controlled at about 6.7, the temperature was maintained at 35° C., and the dissolved oxygen was controlled at 25-30%. After the glucose in the culture medium was depleted, an 80% (m/v) of glucose solution was fed to maintain the glucose concentration in the fermentation medium at 0.1-5 g/L; 12-16 h later, introduction of sterile air was stopped to carry out anaerobic fermentation; the total fermentation cycle was 40 h.

The seed culture medium comprised 60-90 g/L glucose, 5 g/L yeast powder, 4 g/L $K_2HPO_4$, 2.5 g/L $(NH_4)_2SO_4$, 2 g/L citric acid, 1-3 mg/L $MgSO_4 \cdot 7H_2O$, 1-3 mg/L each of $V_{B1}$, $V_{B3}$, $V_{B5}$, $V_{B12}$, and $V_H$, 2.8 mg/L/L $FeSO_4 \cdot 7H_2O$ and 1.2 mg/L $MnSO_4$.

The fermentation medium consisted of 30 g/L glucose, 2 g/L yeast powder, 7 g/L $K_2HPO_4$, 3 g/L $(NH_4)_2SO_4$, 2 g/L citric acid, 1 g/L $MgSO_4 \cdot 7H_2O$, 30 mg/L $FeSO_4 \cdot 7H_2O$, 10 mg/L $MnSO_4$, 1 mg/L each of $V_{B1}$, $V_{B3}$, $V_{B5}$, $V_{B12}$, and $V_H$, pH 6.5-7.0.

TABLE 7

Comparison of parameters between aerobic fermentation and aerobic-anaerobic two-stage fermentation in fermentor

| Strain | Aerobic fermentation | | | Aerobic-anaerobic two-stage fermentation | | |
|---|---|---|---|---|---|---|
| | L-valine titer (g/L) | Sugar-acid conversion rate (%) | Productivity (g/L/h) | L-valine titer (g/L) | Sugar-acid conversion rate (%) | Productivity (g/L/h) |
| VXR05 | 80.2 | 30.6 | 2.0 | 80.8 | 40.7 | 2.0 |

As can be seen from Table 7, the L-valine titer reached 80.2 g/L and the sugar-acid conversion rate was 30.6% after the strain VXR05 underwent aerobic culture for 40 h in a 5 L fermentor. Adopting the Aerobic-anaerobic two-stage process, the L-valine titer reached 80.8 g/L, and the sugar-acid conversion rate was increased to 40.7%, 33% higher than that in aerobic fermentation.

Although the disclosure has been disclosed in terms of prefer embodiments, they are not intended to limit the disclosure, and various changes or modification may be made by those skilled in the art without departing from the spirit and scope of the disclosure. Therefore, the scope of the disclosure should be determined by the claims.

What is claimed is:

1. A genetically engineered strain for producing L-valine, comprising:
   E. coli W3110 as taken as a starting strain;
   a gene alsS encoding acetolactate synthase of *Bacillus subtilis* is inserted into a genome of the *E. coli* W3110 and subjected to overexpression;
   a mutant gene spoT$^M$ is inserted into the genome of the *E. coli* W3110 and subjected to overexpression, wherein the mutant gene spoT$^M$ encodes a mutant R290E/K292D of the wild-type *E. coli* ppGpp 3'-pyrophosphate hydrolase as shown in SEQ ID NO: 63;
   a gene ldhA encoding lactate dehydrogenase, a gene pflB encoding pyruvate formate lyase I, and genes frdA, frdB, frdC and frdD for four subunits of fumarate reductase are deleted from the genome of the *E. coli* W3110;
   a gene bcd encoding leucine dehydrogenase of *Bacillus subtilis* replaces a gene ilvE encoding branched-chain amino acid transaminase of the *E. coli* W3110; and
   a mutant gene ilvC$^M$ replaces a gene ilvC encoding acetohydroxy acid isomeroreductase of the *E. coli* W3110, wherein the mutant gene ilvC$^M$ encodes a mutant L67E/R68F/K75E of the wild-type *E. coli* acetohydroxy acid isomeroreductase as shown in SEQ ID NO: 65.

2. The genetically engineered strain according to claim 1, wherein
   the gene alsS encoding the acetolactate synthase is inserted into an *E. coli* pseudogene ydeU site and controlled by an *E. coli* promoter P$_{trc}$; and
   the mutant gene spoT$^M$ encoding the ppGpp 3'-pyrophosphate hydrolase mutant R290E/K292D is inserted into an *E. coli* pseudogene yeeP site and controlled by the *E. coli* promoter P$_{trc}$.

3. The genetically engineered strain according to claim 1, wherein the mutant gene spoT$^M$ has the nucleotide sequence as shown in SEQ ID NO: 1 and encodes the ppGpp 3'-pyrophosphate hydrolase mutant R290E/K292D as shown in SEQ ID NO: 64.

4. The genetically engineered strain according to claim 1, wherein the mutant gene ilvC$^M$ has the nucleotide sequence as shown in SEQ ID NO: 2 and encodes the acetohydroxy acid isomeroreductase mutant L67E/R68F/K75E as shown in SEQ ID NO: 66.

5. A method for producing L-valine by a fermentation comprising the step of using the genetically engineered strain according to claim 1 to synthesize L-valine.

6. A method for producing L-valine by a fermentation using the genetically engineered strain according to claim 1, wherein the method is a two-stage dissolved oxygen control process, comprising: performing an aerobic fermentation in a first stage of fermentation, and then performing an anaerobic fermentation in a middle stage and later stage of fermentation and wherein the genetically engineered strain according to claim 1 is provided in the first, middle and later stages of fermentation.

7. The method according to claim 6, comprising:
subjecting the genetically engineered strain to an activation to prepare a seed fermentation broth,
inoculating the seed fermentation broth into a triangular flask filled with a fermentation medium with an inoculum size of 10-15%, and subjecting to a shake cultivation at 37° C. and 200 r/min to obtain a bacterial solution,
after 12-16 h, transferring the bacterial solution to a 30 mL sealed flask isolated from air, and subjecting the 30 mL sealed flask to the shake cultivation at 37° C. and 200 r/min for 8-12 h,
wherein the fermentation medium comprises 18 g/L glucose, 1 g/L yeast powder, 2 g/L peptone, 2 g/L $KH_2PO_4$, 1 g/L sodium citrate, 0.7 g/L $MgSO_4 \cdot 7H_2O$, 100 mg/L $FeSO_4 \cdot 7H_2O$, 100 mg/L $MnSO_4 \cdot H_2O$, 0.8 mg/L $V_{B1}$, 0.3 mg/L $V_H$, 20 mL/L phenol red, and two droplets of a defoaming agent, and the fermentation medium has an initial pH of 7.0-7.2.

8. The method according to claim 6, comprising:
subjecting the genetically engineered strain to an activation on a slant for two generations,
inoculating the genetically engineered strain activated into a fermentation medium with an inoculum size of 15-20% to perform a fermentation, wherein in the fermentation, pH is controlled at about 6.7, a temperature is maintained at 35° C., and dissolved oxygen is controlled at 25-30%;
after glucose in the fermentation medium is depleted, feeding an 80% m/v glucose solution to maintain a glucose concentration in the fermentation medium at 0.1-5 g/L;
12-16 h later, stopping an introduction of sterile air and starting to carry out an anaerobic fermentation,
wherein the fermentation medium comprises 30 g/L glucose, 2 g/L yeast powder, 7 g/L $K_2HPO_4$, 3 g/L $(NH_4)_2SO_4$, 2 g/L citric acid, 1 g/L $MgSO_4 \cdot 7H_2O$, 30 mg/L $FeSO_4 \cdot 7H_2O$, 10 mg/L $MnSO_4$, 1 mg/L each of $V_{B1}$, $V_{B3}$, $V_{B5}$, $V_{B12}$, and $V_H$, and the fermentation medium has an initial pH of 6.5-7.0.

9. The method of producing L-valine according to claim 5, wherein
the gene alsS encoding the acetolactate synthase is inserted into a pseudogene ydeU site and controlled by an *E. coli* promoter $P_{trc}$; and
the mutant gene $spoT^M$ encoding the ppGpp 3'-pyrophosphate hydrolase mutant R290E/K292D is inserted into a pseudogene yeeP site and controlled by the *E. coli* promoter $P_{trc}$.

10. The method of producing L-valine according to claim 5, wherein the mutant gene $spoT^M$ encoding the ppGpp 3'-pyrophosphate hydrolase mutant R290E/K292D has the nucleotide sequence as shown in SEQ ID NO: 1.

11. The method of producing L-valine according to claim 5, wherein the mutant gene $ilvC^M$ encoding the acetohydroxy acid isomeroreductase mutant L67E/R68F/K75E has the nucleotide sequence as shown in SEQ ID NO: 2.

12. The method according to claim 6, wherein
the gene alsS encoding the acetolactate synthase is inserted into a pseudogene ydeU site and controlled by an *E. coli* promoter $P_{trc}$; and
the mutant gene $spoT^M$ encoding the ppGpp 3'-pyrophosphate hydrolase mutant R290E/K292D is inserted into a pseudogene yeeP site and controlled by the *E. coli* promoter $P_{trc}$.

13. The method according to claim 6, wherein the mutant gene $spoT^M$ encoding the ppGpp 3'-pyrophosphate hydrolase mutant R290E/K292D has the nucleotide sequence as shown in SEQ ID NO: 1.

14. The method according to claim 6, wherein the mutant gene $ilvC^M$ encoding the acetohydroxy acid isomeroreductase mutant L67E/R68F/K75E has the nucleotide sequence as shown in SEQ ID NO: 2.

\* \* \* \* \*

SEQUENCE LISTING

<160> NUMBER OF SEQ ID NOS: 66

<210> SEQ ID NO 1
<211> LENGTH: 2109
<212> TYPE: DNA
<213> ORGANISM: Artificial Sequence
<220> FEATURE:
<223> OTHER INFORMATION: mutant gene spoT encoding the ppGpp 3'-pyrophosphate hydrolase mutant R290E/K292D

<400> SEQUENCE: 1

```
ttgtatctgt tgaaagcct gaatcaactg attcaaacct acctgccgga agaccaaatc      60
aagcgtctgc ggcaggcgta tctcgttgca cgtgatgctc acgaggggca aacacgttca     120
agcggtgaac cctatatcac gcacccggta gcggttgcct gcattctggc cgagatgaaa     180
ctcgactatg aaacgctgat ggcggcgctg ctgcatgacg tgattgaaga tactcccgcc     240
acctaccagg atatggaaca gcttttttggt aaaagcgtcg ccgagctggt agaggggtg      300 tcgaaacttg ataaactcaa gttccgcgat aagaaagagg cgcaggccga aaactttcgc     360
aagatgatta tggcgatggt gcaggatatc cgcgtcatcc tcatcaaact tgccgaccgt     420
acccacaaca tgcgcacgct gggctcactt cgcccggaca aacgtcgccg catcgcccgt     480
gaaactctcg aaatttatag cccgctggcg caccgtttag gtatccacca cattaaaacc     540
gaactcgaag agctgggttt tgaggcgctg tatcccaacc gttatcgcgt aatcaaagaa     600
gtggtgaaag ccgcgcgcgg caaccgtaaa gagatgatcc agaagattct ttctgaaatc     660
gaagggcgtt tgcaggaagc gggaatacccg tgccgcgtca gtggtcgcga agcatctt      720 tattcgattt actgcaaaat ggtgctcaaa gagcagcgtt tcactcgat catggacatc      780 tacgctttcc gcgtgatcgt caatgattct gacacctgtt atcgcgtgct gggccagatg     840
cacagcctgt acaagccgcg tccgggcgaa gtggatgact atatcgccat tccaaaagcg     900
aacggctatc agtctttgca cacctcgatg atcggccgc acggtgtgcc ggttgaggtc      960
cagatccgta ccgaagatat ggaccagatg gcggagatgg tgttgccgc gcactgggct    1020 tataaagagc acggcgaaac cagtactacc gcacaaatcc gcgcccagcg ctggatgcaa    1080
agcctgctgg agctgcaaca gagcgccggt agttcgtttg aatttatcga gagcgttaaa    1140
tccgatctct ccccggatga gatttacgtt ttcacaccgg aagggcgcat tgtcgagctg    1200
cctgccggtg caacgcccgt cgacttcgct tatgcagtgc ataccgatat cggtcatgcc    1260
tgcgtgggcg cacgcgttga ccgccagcct tacccgctgt cgcagccgct taccagcggt    1320
caaaccgttg aaatcattac cgctccgggc gctcgcccga atgccgcttg gctgaactttt   1380 gtcgttagct cgaaagcgcg cgccaaaatt cgtcagttgc tgaaaaacct caagcgtgat    1440
gattctgtaa gcctgggccg tcgtctgctc aaccatgctt tgggtggtag ccgtaagctg    1500
```

| | |
|---|---:|
| aatgaaatcc cgcaggaaaa tattcagcgc gagctggatc gcatgaagct ggcaacgctt | 1560 |
| gacgatctgc tggcagaaat cggacttggt aacgcaatga gcgtggtggt cgcgaaaaat | 1620 |
| ctgcaacatg gggacgcctc cattccaccg gcaacccaaa gccacggaca tctgcccatt | 1680 |
| aaaggtgccg atggcgtgct gatcaccttt gcgaaatgct gccgccctat tcctggcgac | 1740 |
| ccgattatcg cccacgtcag ccccggtaaa ggtctggtga tccaccatga atcctgccgt | 1800 |
| aatatccgtg gctaccagaa agagccgag aagtttatgg ctgtggaatg ggataaagag | 1860 |
| acggcgcagg agttcatcac cgaaatcaag gtggagatgt caatcatca gggtgcgctg | 1920 |
| gcaaacctga cggcggcaat taacaccacg acttcgaata ttcaaagttt gaatacggaa | 1980 |
| gagaaagatg gtcgcgtcta cagcgccttt attcgtctga ccgctcgtga ccgtgtgcat | 2040 |
| ctggcgaata tcatgcgcaa aatccgcgtg atgccagacg tgattaaagt cacccgaaac | 2100 |
| cgaaattaa | 2109 |

<210> SEQ ID NO 2
<211> LENGTH: 1476
<212> TYPE: DNA
<213> ORGANISM: Artificial Sequence
<220> FEATURE:
<223> OTHER INFORMATION: mutant gene encoding the acetohydroxy acid
      isomeroreductase mutant L67E/R68F/K75E

<400> SEQUENCE: 2

| | |
|---|---:|
| atggctaact acttcaatac actgaatctg cgccagcagc tggcacagct gggcaaatgt | 60 |
| cgctttatgg ccgcgatga attcgccgat ggcgcgagct accttcaggg taaaaaagta | 120 |
| gtcatcgtcg gctgtggcgc acagggtctg aaccagggcc tgaacatgcg tgattctggt | 180 |
| ctcgatatct cctacgctga gtttaaagaa gcgattgccg aggagcgcgc gtcctggcgt | 240 |
| aaagcgaccg aaaatggttt taaagtgggt acttacgaag aactgatccc acaggcggat | 300 |
| ctggtgatta acctgacgcc ggacaagcag cactctgatg tagtgcgcac cgtacagcca | 360 |
| ctgatgaaag acggcgcggc gctgggctac tcgcacggtt tcaacatcgt cgaagtgggc | 420 |
| gagcagatcc gtaaagatat caccgtagtg atggttgcgc cgaaatgccc aggcaccgaa | 480 |
| gtgcgtgaag agtacaaacg tgggttcggc gtaccgacgc tgattgccgt tcacccggaa | 540 |
| aacgatccga aggcgaagg catggcgatt gccaaagcct gggcggctgc aaccggtggt | 600 |
| caccgtgcgg gtgtgctgga atcgtcctt gttgcggaag tgaaatctga cctgatgggc | 660 |
| gagcaaacca tcctgtgcgg tatgttgcag gctggctctc tgctgtgctt cgacaagctg | 720 |
| gtggaagaag gtaccgatcc agcatacgca gaaaaactga ttcagttcgg ttgggaaacc | 780 |
| atcaccgaag cactgaaaca gggcggcatc accctgatga tggaccgtct ctctaacccg | 840 |
| gcgaaactgc gtgcttatgc gctttctgaa cagctgaaag atcatggc accctgttc | 900 |
| cagaaacata tggacgacat catctccggc gaattctctt ccggtatgat ggcggactgg | 960 |
| gccaacgatg ataagaaact gctgacctgg cgtgaagaga ccgcaaaac cgcgtttgaa | 1020 |
| accgcgccgc agtatgaagg caaatcggc gagcaggagt acttcgataa aggcgtactg | 1080 |
| atgattgcga tggtgaaagc gggcgttgaa ctggcgttcg aaaccatggt cgattccggc | 1140 |
| atcattgaag agtctgcata ttatgaatca ctgcacgagc tgccgctgat tgccaacacc | 1200 |
| atcgcccgta agcgtctgta cgaaatgaac gtggttatct ctgataccgc tgagtacggt | 1260 |
| aactatctgt tctcttacgc ttgtgtgccg ttgctgaaac cgtttatggc agagctgcaa | 1320 |
| ccgggcgacc tgggtaaagc tattccggaa ggcgcggtag ataacgggca actgcgtgat | 1380 |

```
gtgaacgaag cgattcgcag ccatgcgatt gagcaggtag gtaagaaact gcgcggctat      1440
atgacagata tgaaacgtat tgctgttgcg ggttaa                                1476

<210> SEQ ID NO 3
<211> LENGTH: 25
<212> TYPE: DNA
<213> ORGANISM: Artificial Sequence
<220> FEATURE:
<223> OTHER INFORMATION: Primer sequence is synthesized

<400> SEQUENCE: 3
ttgtatctgt ttgaaagcct gaatc                                              25

<210> SEQ ID NO 4
<211> LENGTH: 39
<212> TYPE: DNA
<213> ORGANISM: Artificial Sequence
<220> FEATURE:
<223> OTHER INFORMATION: Primer sequence is synthesized

<400> SEQUENCE: 4
tcgcttttgg aatggcgata tagtcatcca cttcgcccg                               39

<210> SEQ ID NO 5
<211> LENGTH: 39
<212> TYPE: DNA
<213> ORGANISM: Artificial Sequence
<220> FEATURE:
<223> OTHER INFORMATION: Primer sequence is synthesized

<400> SEQUENCE: 5
cgggcgaagt ggatgactat atcgccattc caaaagcga                               39

<210> SEQ ID NO 6
<211> LENGTH: 22
<212> TYPE: DNA
<213> ORGANISM: Artificial Sequence
<220> FEATURE:
<223> OTHER INFORMATION: Primer sequence is synthesized

<400> SEQUENCE: 6
ttaatttcgg tttcgggtga ct                                                 22

<210> SEQ ID NO 7
<211> LENGTH: 21
<212> TYPE: DNA
<213> ORGANISM: Artificial Sequence
<220> FEATURE:
<223> OTHER INFORMATION: Primer sequence is synthesized

<400> SEQUENCE: 7
ctgcgtaata gcataagcgg g                                                  21

<210> SEQ ID NO 8
<211> LENGTH: 77
<212> TYPE: DNA
<213> ORGANISM: Artificial Sequence
<220> FEATURE:
<223> OTHER INFORMATION: Primer sequence is synthesized

<400> SEQUENCE: 8
aattgttatc cgctcacaat tccacacatt atacgagccg gatgattaat tgtcaagcta        60
ttcatttgaa ccgtgcc                                                       77
```

<210> SEQ ID NO 9
<211> LENGTH: 83
<212> TYPE: DNA
<213> ORGANISM: Artificial Sequence
<220> FEATURE:
<223> OTHER INFORMATION: Primer sequence is synthesized

<400> SEQUENCE: 9
tccggctcgt ataatgtgtg gaattgtgag cggataacaa tttcacacag gaaacagacc    60
ttgacaaaag caacaaaaga aca                                            83

<210> SEQ ID NO 10
<211> LENGTH: 45
<212> TYPE: DNA
<213> ORGANISM: Artificial Sequence
<220> FEATURE:
<223> OTHER INFORMATION: Primer sequence is synthesized

<400> SEQUENCE: 10
attcccccac aggctaaggt ctagagagct ttcgttttca tgagt                    45

<210> SEQ ID NO 11
<211> LENGTH: 45
<212> TYPE: DNA
<213> ORGANISM: Artificial Sequence
<220> FEATURE:
<223> OTHER INFORMATION: Primer sequence is synthesized

<400> SEQUENCE: 11
actcatgaaa acgaaagctc tctagacctt agcctgtggg ggaat                    45

<210> SEQ ID NO 12
<211> LENGTH: 22
<212> TYPE: DNA
<213> ORGANISM: Artificial Sequence
<220> FEATURE:
<223> OTHER INFORMATION: Primer sequence is synthesized

<400> SEQUENCE: 12
atgtcgtgag cgtggtattg tc                                             22

<210> SEQ ID NO 13
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 13
agtcctaggt ataatactag tgttcgggtt gataacattg ggtttttagag ctagaa       56

<210> SEQ ID NO 14
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 14
ttctagctct aaaacccaat gttatcaacc cgaacactag tattataccct aggact       56

<210> SEQ ID NO 15
<211> LENGTH: 22
<212> TYPE: DNA
<213> ORGANISM: Artificial Sequence

```
<220> FEATURE:
<223> OTHER INFORMATION: Primer sequence is synthesized

<400> SEQUENCE: 15
actgcgtaat agcataagcg gg                                            22

<210> SEQ ID NO 16
<211> LENGTH: 19
<212> TYPE: DNA
<213> ORGANISM: Artificial Sequence
<220> FEATURE:
<223> OTHER INFORMATION: Primer sequence is synthesized

<400> SEQUENCE: 16
tgcttgccga cccctgaga                                                19

<210> SEQ ID NO 17
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 17
ggtcaggagg taacttatca gcg                                           23

<210> SEQ ID NO 18
<211> LENGTH: 74
<212> TYPE: DNA
<213> ORGANISM: Artificial Sequence
<220> FEATURE:
<223> OTHER INFORMATION: Primer sequence is synthesized

<400> SEQUENCE: 18
aattgttatc cgctcacaat tccacacatt atacgagccg gatgattaat tgtcaaatgg   60
cagggctccg tttt                                                     74

<210> SEQ ID NO 19
<211> LENGTH: 85
<212> TYPE: DNA
<213> ORGANISM: Artificial Sequence
<220> FEATURE:
<223> OTHER INFORMATION: Primer sequence is synthesized

<400> SEQUENCE: 19
tccggctcgt ataatgtgtg gaattgtgag cggataacaa tttcacacag gaaacagacc   60
ttgtatctgt ttgaaagcct gaatc                                         85

<210> SEQ ID NO 20
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 20
agacccgttt agaggcccca aggggttatg ctagttaatt tcggtttcgg gtgact       56

<210> SEQ ID NO 21
<211> LENGTH: 59
<212> TYPE: DNA
<213> ORGANISM: Artificial Sequence
<220> FEATURE:
<223> OTHER INFORMATION: Primer sequence is synthesized
```

<400> SEQUENCE: 21
tggggcctct aaacgggtct tgagggtttt tttggaactg gattttcttc tgaacctgt        59

<210> SEQ ID NO 22
<211> LENGTH: 19
<212> TYPE: DNA
<213> ORGANISM: Artificial Sequence
<220> FEATURE:
<223> OTHER INFORMATION: Primer sequence is synthesized

<400> SEQUENCE: 22
acgatgtcag cagccagca                                                    19

<210> SEQ ID NO 23
<211> LENGTH: 59
<212> TYPE: DNA
<213> ORGANISM: Artificial Sequence
<220> FEATURE:
<223> OTHER INFORMATION: Primer sequence is synthesized

<400> SEQUENCE: 23
agtcctaggt ataatactag tacagaatat tcgcgaaaaa acgggtttta gagctagaa        59

<210> SEQ ID NO 24
<211> LENGTH: 59
<212> TYPE: DNA
<213> ORGANISM: Artificial Sequence
<220> FEATURE:
<223> OTHER INFORMATION: Primer sequence is synthesized

<400> SEQUENCE: 24
ttctagctct aaaacccgtt ttttcgcgaa tattctgtac tagtattata cctaggact        59

<210> SEQ ID NO 25
<211> LENGTH: 21
<212> TYPE: DNA
<213> ORGANISM: Artificial Sequence
<220> FEATURE:
<223> OTHER INFORMATION: Primer sequence is synthesized

<400> SEQUENCE: 25
ggaacgatac agcgaaacca c                                                 21

<210> SEQ ID NO 26
<211> LENGTH: 79
<212> TYPE: DNA
<213> ORGANISM: Artificial Sequence
<220> FEATURE:
<223> OTHER INFORMATION: Primer sequence is synthesized

<400> SEQUENCE: 26
aattgttatc cgctcacaat tccacacatt atacgagccg gatgattaat tgtcaagctt        60
tcttcgtggt catttttat                                                    79

<210> SEQ ID NO 27
<211> LENGTH: 46
<212> TYPE: DNA
<213> ORGANISM: Artificial Sequence
<220> FEATURE:
<223> OTHER INFORMATION: Primer sequence is synthesized

<400> SEQUENCE: 27
ccacagtgta ttaagcagac gttaaataca aaaaatggga cggcac                      46

-continued

```
<210> SEQ ID NO 28
<211> LENGTH: 22
<212> TYPE: DNA
<213> ORGANISM: Artificial Sequence
<220> FEATURE:
<223> OTHER INFORMATION: Primer sequence is synthesized

<400> SEQUENCE: 28
tgggagtcag atactttcgg gt                                              22

<210> SEQ ID NO 29
<211> LENGTH: 86
<212> TYPE: DNA
<213> ORGANISM: Artificial Sequence
<220> FEATURE:
<223> OTHER INFORMATION: Primer sequence is synthesized

<400> SEQUENCE: 29
tccggctcgt ataatgtgtg gaattgtgag cggataacaa tttcacacag gaaacagacc     60
tctgaagaat acacacatta ggagga                                          86

<210> SEQ ID NO 30
<211> LENGTH: 46
<212> TYPE: DNA
<213> ORGANISM: Artificial Sequence
<220> FEATURE:
<223> OTHER INFORMATION: Primer sequence is synthesized

<400> SEQUENCE: 30
gtgccgtccc atttttgta tttaacgtct gcttaataca ctgtgg                     46

<210> SEQ ID NO 31
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 31
agtcctaggt ataatactag tcgccaaaat ctatcgcttc cgttttagag ctagaa         56

<210> SEQ ID NO 32
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 32
ttctagctct aaaacggaag cgatagattt tggcgactag tattatacct aggact         56

<210> SEQ ID NO 33
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 33
tctaccgaca cctgattacg cac                                             23

<210> SEQ ID NO 34
<211> LENGTH: 79
<212> TYPE: DNA
<213> ORGANISM: Artificial Sequence
<220> FEATURE:
```

```
<223> OTHER INFORMATION: Primer sequence is synthesized

<400> SEQUENCE: 34
aattgttatc cgctcacaat tccacacatt atacgagccg gatgattaat tgtcaaatgg      60
tgattcctcg tgatgttgt                                                  79

<210> SEQ ID NO 35
<211> LENGTH: 45
<212> TYPE: DNA
<213> ORGANISM: Artificial Sequence
<220> FEATURE:
<223> OTHER INFORMATION: Primer sequence is synthesized

<400> SEQUENCE: 35
acttgatgac cgccctctgt attttcggtc ttctctctct gattt                     45

<210> SEQ ID NO 36
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 36
ataacaatgg gcaaaaatac ggt                                             23

<210> SEQ ID NO 37
<211> LENGTH: 83
<212> TYPE: DNA
<213> ORGANISM: Artificial Sequence
<220> FEATURE:
<223> OTHER INFORMATION: Primer sequence is synthesized

<400> SEQUENCE: 37
tccggctcgt ataatgtgtg gaattgtgag cggataacaa tttcacacag gaaacagacc     60
atggctaact acttcaatac act                                             83

<210> SEQ ID NO 38
<211> LENGTH: 48
<212> TYPE: DNA
<213> ORGANISM: Artificial Sequence
<220> FEATURE:
<223> OTHER INFORMATION: Primer sequence is synthesized

<400> SEQUENCE: 38
gcgcgctcct cggcaatcgc ttctttaaac tcagcgtagg agatatcg                  48

<210> SEQ ID NO 39
<211> LENGTH: 54
<212> TYPE: DNA
<213> ORGANISM: Artificial Sequence
<220> FEATURE:
<223> OTHER INFORMATION: Primer sequence is synthesized

<400> SEQUENCE: 39
tggtctcgat atctcctacg ctgagtttaa agaagcgatt gccgaggagc gcgc           54

<210> SEQ ID NO 40
<211> LENGTH: 81
<212> TYPE: DNA
<213> ORGANISM: Artificial Sequence
<220> FEATURE:
<223> OTHER INFORMATION: Primer sequence is synthesized

<400> SEQUENCE: 40
```

```
caccgacaaa caacagataa aacgaaaggc ccagtctttc gactgagcct ttcgttttat    60
ttgtcggggt gagggcatca g                                              81

<210> SEQ ID NO 41
<211> LENGTH: 83
<212> TYPE: DNA
<213> ORGANISM: Artificial Sequence
<220> FEATURE:
<223> OTHER INFORMATION: Primer sequence is synthesized

<400> SEQUENCE: 41
aaagactggg cctttcgttt tatctgttgt ttgtcggtga acgctctcct gagtaggaca    60
aatccctctc ccacagggag agg                                            83

<210> SEQ ID NO 42
<211> LENGTH: 45
<212> TYPE: DNA
<213> ORGANISM: Artificial Sequence
<220> FEATURE:
<223> OTHER INFORMATION: Primer sequence is synthesized

<400> SEQUENCE: 42
aaatcagaga gagaagaccg aaaatacaga gggcggtcat caagt                    45

<210> SEQ ID NO 43
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 43
agtcctaggt ataatactag ttggtcgcga gtggttgata agttttagag ctagaa        56

<210> SEQ ID NO 44
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 44
ttctagctct aaaacttatc aaccactcgc gaccaactag tattatacct aggact        56

<210> SEQ ID NO 45
<211> LENGTH: 18
<212> TYPE: DNA
<213> ORGANISM: Artificial Sequence
<220> FEATURE:
<223> OTHER INFORMATION: Primer sequence is synthesized

<400> SEQUENCE: 45
gcggctggga tgtgaaag                                                  18

<210> SEQ ID NO 46
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 46
gaatacgcca aaggactcgt tcacct                                         26
```

<210> SEQ ID NO 47
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 47
tttggcgtat tccgtcgcct gtctgc                                  26

<210> SEQ ID NO 48
<211> LENGTH: 19
<212> TYPE: DNA
<213> ORGANISM: Artificial Sequence
<220> FEATURE:
<223> OTHER INFORMATION: Primer sequence is synthesized

<400> SEQUENCE: 48
atgtctgttt tgcggtcgc                                          19

<210> SEQ ID NO 49
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 49
agtcctaggt ataatactag taaacgatga cggcagccgc cgttttagag ctagaa  56

<210> SEQ ID NO 50
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 50
ttctagctct aaaacggcgg ctgccgtcat cgtttactag tattatacct aggact  56

<210> SEQ ID NO 51
<211> LENGTH: 19
<212> TYPE: DNA
<213> ORGANISM: Artificial Sequence
<220> FEATURE:
<223> OTHER INFORMATION: Primer sequence is synthesized

<400> SEQUENCE: 51
tcggcaacat tatcggtgg                                          19

<210> SEQ ID NO 52
<211> LENGTH: 25
<212> TYPE: DNA
<213> ORGANISM: Artificial Sequence
<220> FEATURE:
<223> OTHER INFORMATION: Primer sequence is synthesized

<400> SEQUENCE: 52
ggttcattta cggcaacgca ggatg                                   25

<210> SEQ ID NO 53
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 53
cgtaaatgaa ccgtgaaatg ctgctc                                          26

<210> SEQ ID NO 54
<211> LENGTH: 20
<212> TYPE: DNA
<213> ORGANISM: Artificial Sequence
<220> FEATURE:
<223> OTHER INFORMATION: Primer sequence is synthesized

<400> SEQUENCE: 54
ggcgataggt caccacttcc                                                 20

<210> SEQ ID NO 55
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 55
agtcctaggt ataatactag ttgttctctg gcgacccgat cgttttagag ctagaa         56

<210> SEQ ID NO 56
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 56
ttctagctct aaaacgatcg ggtcgccaga gaacaactag tattatacct aggact         56

<210> SEQ ID NO 57
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 57
ggtcttcttc ggtatcagca aca                                             23

<210> SEQ ID NO 58
<211> LENGTH: 45
<212> TYPE: DNA
<213> ORGANISM: Artificial Sequence
<220> FEATURE:
<223> OTHER INFORMATION: Primer sequence is synthesized

<400> SEQUENCE: 58
tagcagccag accgtagaaa acccttcgtg cccttgtcaa aaact                     45

<210> SEQ ID NO 59
<211> LENGTH: 45
<212> TYPE: DNA
<213> ORGANISM: Artificial Sequence
<220> FEATURE:
<223> OTHER INFORMATION: Primer sequence is synthesized

<400> SEQUENCE: 59 agttttttgac aagggcacga agggttttct acggtctggc tgcta                    45

<210> SEQ ID NO 60

-continued

```
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 60
acgccagtaa atgttttgct gac                                              23

<210> SEQ ID NO 61
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 61
agtcctaggt ataatactag tcccaaccga atgacccaa cgttttagag ctagaa           56

<210> SEQ ID NO 62
<211> LENGTH: 56
<212> TYPE: DNA
<213> ORGANISM: Artificial Sequence
<220> FEATURE:
<223> OTHER INFORMATION: Primer sequence is synthesized

<400> SEQUENCE: 62
ttctagctct aaaacgttgg gtcatttcgg ttgggactag tattatacct aggact          56

<210> SEQ ID NO 63
<211> LENGTH: 702
<212> TYPE: PRT
<213> ORGANISM: Escherichia coli

<400> SEQUENCE: 63
```

Met Tyr Leu Phe Glu Ser Leu Asn Gln Leu Ile Gln Thr Tyr Leu Pro
1               5                   10                  15

Glu Asp Gln Ile Lys Arg Leu Arg Gln Ala Tyr Leu Val Ala Arg Asp
            20                  25                  30

Ala His Glu Gly Gln Thr Arg Ser Ser Gly Glu Pro Tyr Ile Thr His
        35                  40                  45

Pro Val Ala Val Ala Cys Ile Leu Ala Glu Met Lys Leu Asp Tyr Glu
    50                  55                  60

Thr Leu Met Ala Ala Leu Leu His Asp Val Ile Glu Asp Thr Pro Ala
65                  70                  75                  80

Thr Tyr Gln Asp Met Glu Gln Leu Phe Gly Lys Ser Val Ala Glu Leu
                85                  90                  95

Val Glu Gly Val Ser Lys Leu Asp Lys Leu Lys Phe Arg Asp Lys Lys
            100                 105                 110

Glu Ala Gln Ala Glu Asn Phe Arg Lys Met Ile Met Ala Met Val Gln
        115                 120                 125

Asp Ile Arg Val Ile Leu Ile Lys Leu Ala Asp Arg Thr His Asn Met
    130                 135                 140

Arg Thr Leu Gly Ser Leu Arg Pro Asp Lys Arg Arg Arg Ile Ala Arg
145                 150                 155                 160

Glu Thr Leu Glu Ile Tyr Ser Pro Leu Ala His Arg Leu Gly Ile His
                165                 170                 175

His Ile Lys Thr Glu Leu Glu Glu Leu Gly Phe Glu Ala Leu Tyr Pro
            180                 185                 190

Asn Arg Tyr Arg Val Ile Lys Glu Val Val Lys Ala Ala Arg Gly Asn

```
                195                 200                 205
Arg Lys Glu Met Ile Gln Lys Ile Leu Ser Glu Ile Glu Gly Arg Leu
210                 215                 220
Gln Glu Ala Gly Ile Pro Cys Arg Val Ser Gly Arg Glu Lys His Leu
225                 230                 235                 240
Tyr Ser Ile Tyr Cys Lys Met Val Leu Lys Glu Gln Arg Phe His Ser
                245                 250                 255
Ile Met Asp Ile Tyr Ala Phe Arg Val Ile Val Asn Asp Ser Asp Thr
            260                 265                 270
Cys Tyr Arg Val Leu Gly Gln Met His Ser Leu Tyr Lys Pro Arg Pro
        275                 280                 285
Gly Arg Val Lys Asp Tyr Ile Ala Ile Pro Lys Ala Asn Gly Tyr Gln
    290                 295                 300
Ser Leu His Thr Ser Met Ile Gly Pro His Gly Val Pro Val Glu Val
305                 310                 315                 320
Gln Ile Arg Thr Glu Asp Met Asp Gln Met Ala Glu Met Gly Val Ala
                325                 330                 335
Ala His Trp Ala Tyr Lys Glu His Gly Glu Thr Ser Thr Thr Ala Gln
            340                 345                 350
Ile Arg Ala Gln Arg Trp Met Gln Ser Leu Leu Glu Leu Gln Gln Ser
        355                 360                 365
Ala Gly Ser Ser Phe Glu Phe Ile Glu Ser Val Lys Ser Asp Leu Phe
    370                 375                 380
Pro Asp Glu Ile Tyr Val Phe Thr Pro Glu Gly Arg Ile Val Glu Leu
385                 390                 395                 400
Pro Ala Gly Ala Thr Pro Val Asp Phe Ala Tyr Ala Val His Thr Asp
                405                 410                 415
Ile Gly His Ala Cys Val Gly Ala Arg Val Asp Arg Gln Pro Tyr Pro
            420                 425                 430
Leu Ser Gln Pro Leu Thr Ser Gly Gln Thr Val Glu Ile Ile Thr Ala
        435                 440                 445
Pro Gly Ala Arg Pro Asn Ala Ala Trp Leu Asn Phe Val Val Ser Ser
    450                 455                 460
Lys Ala Arg Ala Lys Ile Arg Gln Leu Leu Lys Asn Leu Lys Arg Asp
465                 470                 475                 480
Asp Ser Val Ser Leu Gly Arg Arg Leu Leu Asn His Ala Leu Gly Gly
                485                 490                 495
Ser Arg Lys Leu Asn Glu Ile Pro Gln Glu Asn Ile Gln Arg Glu Leu
            500                 505                 510
Asp Arg Met Lys Leu Ala Thr Leu Asp Asp Leu Leu Ala Glu Ile Gly
        515                 520                 525
Leu Gly Asn Ala Met Ser Val Val Ala Lys Asn Leu Gln His Gly
    530                 535                 540
Asp Ala Ser Ile Pro Pro Ala Thr Gln Ser His Gly His Leu Pro Ile
545                 550                 555                 560
Lys Gly Ala Asp Gly Val Leu Ile Thr Phe Ala Lys Cys Cys Arg Pro
                565                 570                 575
Ile Pro Gly Asp Pro Ile Ala His Val Ser Pro Gly Lys Gly Leu
            580                 585                 590
Val Ile His His Glu Ser Cys Arg Asn Ile Arg Gly Tyr Gln Lys Glu
        595                 600                 605
Pro Glu Lys Phe Met Ala Val Glu Trp Asp Lys Glu Thr Ala Gln Glu
    610                 615                 620
```

```
Phe Ile Thr Glu Ile Lys Val Glu Met Phe Asn His Gln Gly Ala Leu
625                 630                 635                 640

Ala Asn Leu Thr Ala Ala Ile Asn Thr Thr Thr Ser Asn Ile Gln Ser
            645                 650                 655

Leu Asn Thr Glu Glu Lys Asp Gly Arg Val Tyr Ser Ala Phe Ile Arg
        660                 665                 670

Leu Thr Ala Arg Asp Arg Val His Leu Ala Asn Ile Met Arg Lys Ile
    675                 680                 685

Arg Val Met Pro Asp Val Ile Lys Val Thr Arg Asn Arg Asn
690                 695                 700

<210> SEQ ID NO 64
<211> LENGTH: 702
<212> TYPE: PRT
<213> ORGANISM: Artificial Sequence
<220> FEATURE:
<223> OTHER INFORMATION: ppGpp 3'-pyrophosphate hydrolase mutant
      R290E/K292D

<400> SEQUENCE: 64

Met Tyr Leu Phe Glu Ser Leu Asn Gln Leu Ile Gln Thr Tyr Leu Pro
1               5                   10                  15

Glu Asp Gln Ile Lys Arg Leu Arg Gln Ala Tyr Leu Val Ala Arg Asp
            20                  25                  30

Ala His Glu Gly Gln Thr Arg Ser Ser Gly Glu Pro Tyr Ile Thr His
        35                  40                  45

Pro Val Ala Val Ala Cys Ile Leu Ala Glu Met Lys Leu Asp Tyr Glu
50                  55                  60

Thr Leu Met Ala Ala Leu Leu His Asp Val Ile Glu Asp Thr Pro Ala
65                  70                  75                  80

Thr Tyr Gln Asp Met Glu Gln Leu Phe Gly Lys Ser Val Ala Glu Leu
                85                  90                  95

Val Glu Gly Val Ser Lys Leu Asp Lys Leu Lys Phe Arg Asp Lys Lys
            100                 105                 110

Glu Ala Gln Ala Glu Asn Phe Arg Lys Met Ile Met Ala Met Val Gln
        115                 120                 125

Asp Ile Arg Val Ile Leu Ile Lys Leu Ala Asp Arg Thr His Asn Met
130                 135                 140

Arg Thr Leu Gly Ser Leu Arg Pro Asp Lys Arg Arg Arg Ile Ala Arg
145                 150                 155                 160

Glu Thr Leu Glu Ile Tyr Ser Pro Leu Ala His Arg Leu Gly Ile His
                165                 170                 175

His Ile Lys Thr Glu Leu Glu Glu Leu Gly Phe Glu Ala Leu Tyr Pro
            180                 185                 190

Asn Arg Tyr Arg Val Ile Lys Glu Val Val Lys Ala Ala Arg Gly Asn
        195                 200                 205

Arg Lys Glu Met Ile Gln Lys Ile Leu Ser Glu Ile Glu Gly Arg Leu
210                 215                 220

Gln Glu Ala Gly Ile Pro Cys Arg Val Ser Gly Arg Glu Lys His Leu
225                 230                 235                 240

Tyr Ser Ile Tyr Cys Lys Met Val Leu Lys Glu Gln Arg Phe His Ser
                245                 250                 255

Ile Met Asp Ile Tyr Ala Phe Arg Val Ile Val Asn Asp Ser Asp Thr
            260                 265                 270

Cys Tyr Arg Val Leu Gly Gln Met His Ser Leu Tyr Lys Pro Arg Pro
```

-continued

```
              275                 280                 285
Gly Glu Val Asp Asp Tyr Ile Ala Ile Pro Lys Ala Asn Gly Tyr Gln
         290                 295                 300

Ser Leu His Thr Ser Met Ile Gly Pro His Gly Val Pro Val Glu Val
305                 310                 315                 320

Gln Ile Arg Thr Glu Asp Met Asp Gln Met Ala Glu Met Gly Val Ala
             325                 330                 335

Ala His Trp Ala Tyr Lys Glu His Gly Glu Thr Ser Thr Thr Ala Gln
             340                 345                 350

Ile Arg Ala Gln Arg Trp Met Gln Ser Leu Leu Glu Leu Gln Gln Ser
             355                 360                 365

Ala Gly Ser Ser Phe Glu Phe Ile Glu Ser Val Lys Ser Asp Leu Phe
         370                 375                 380

Pro Asp Glu Ile Tyr Val Phe Thr Pro Glu Gly Arg Ile Val Glu Leu
385                 390                 395                 400

Pro Ala Gly Ala Thr Pro Val Asp Phe Ala Tyr Ala Val His Thr Asp
                 405                 410                 415

Ile Gly His Ala Cys Val Gly Ala Arg Val Asp Arg Gln Pro Tyr Pro
             420                 425                 430

Leu Ser Gln Pro Leu Thr Ser Gly Gln Thr Val Glu Ile Ile Thr Ala
             435                 440                 445

Pro Gly Ala Arg Pro Asn Ala Ala Trp Leu Asn Phe Val Val Ser Ser
         450                 455                 460

Lys Ala Arg Ala Lys Ile Arg Gln Leu Leu Lys Asn Leu Lys Arg Asp
465                 470                 475                 480

Asp Ser Val Ser Leu Gly Arg Arg Leu Leu Asn His Ala Leu Gly Gly
                 485                 490                 495

Ser Arg Lys Leu Asn Glu Ile Pro Gln Glu Asn Ile Gln Arg Glu Leu
             500                 505                 510

Asp Arg Met Lys Leu Ala Thr Leu Asp Asp Leu Leu Ala Glu Ile Gly
             515                 520                 525

Leu Gly Asn Ala Met Ser Val Val Ala Lys Asn Leu Gln His Gly
         530                 535                 540

Asp Ala Ser Ile Pro Pro Ala Thr Gln Ser His Gly His Leu Pro Ile
545                 550                 555                 560

Lys Gly Ala Asp Gly Val Leu Ile Thr Phe Ala Lys Cys Cys Arg Pro
                 565                 570                 575

Ile Pro Gly Asp Pro Ile Ile Ala His Val Ser Pro Gly Lys Gly Leu
             580                 585                 590

Val Ile His His Glu Ser Cys Arg Asn Ile Arg Gly Tyr Gln Lys Glu
             595                 600                 605

Pro Glu Lys Phe Met Ala Val Glu Trp Asp Lys Glu Thr Ala Gln Glu
             610                 615                 620

Phe Ile Thr Glu Ile Lys Val Glu Met Phe Asn His Gln Gly Ala Leu
625                 630                 635                 640

Ala Asn Leu Thr Ala Ala Ile Asn Thr Thr Thr Ser Asn Ile Gln Ser
                 645                 650                 655

Leu Asn Thr Glu Glu Lys Asp Gly Arg Val Tyr Ser Ala Phe Ile Arg
             660                 665                 670

Leu Thr Ala Arg Asp Arg Val His Leu Ala Asn Ile Met Arg Lys Ile
             675                 680                 685

Arg Val Met Pro Asp Val Ile Lys Val Thr Arg Asn Arg Asn
         690                 695                 700
```

<210> SEQ ID NO 65
<211> LENGTH: 491
<212> TYPE: PRT
<213> ORGANISM: Escherichia coli

<400> SEQUENCE: 65

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
```

```
                    370                 375                 380
Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
                420                 425                 430

Lys Pro Phe Met Ala Glu Leu Gln Pro Gly Asp Leu Gly Lys Ala Ile
            435                 440                 445

Pro Glu Gly Ala Val Asp Asn Gly Gln Leu Arg Asp Val Asn Glu Ala
        450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 66
<211> LENGTH: 491
<212> TYPE: PRT
<213> ORGANISM: Artificial Sequence
<220> FEATURE:
<223> OTHER INFORMATION: acetohydroxy acid isomeroreductase mutant L67E/
      R68F/K75E

<400> SEQUENCE: 66

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Lys Val Val Val Gly Cys Gly Ala Gln
            35                  40                  45

Gly Leu Asn Gln Gly Leu Asn Met Arg Asp Ser Gly Leu Asp Ile Ser
        50                  55                  60

Tyr Ala Glu Phe Lys Glu Ala Ile Ala Glu Glu Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
        130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
            195                 200                 205

Ser Phe Val Ala Glu Val Lys Ser Asp Leu Met Gly Glu Gln Thr Ile
        210                 215                 220

Leu Cys Gly Met Leu Gln Ala Gly Ser Leu Leu Cys Phe Asp Lys Leu
225                 230                 235                 240
```

-continued

```
Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
            275                 280                 285

Ser Glu Gln Leu Lys Glu Ile Met Ala Pro Leu Phe Gln Lys His Met
        290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
        370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
            435                 440                 445

Pro Glu Gly Ala Val Asp Asn Gly Gln Leu Arg Asp Val Asn Glu Ala
        450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490
```